United States Patent
Comely et al.

(10) Patent No.: US 11,168,047 B2
(45) Date of Patent: Nov. 9, 2021

(54) COCRYSTAL OF 2-[(1R,6R)-6-ISOPROPENYL-3-METHYLCYCLOHEX-2-EN-1-YL]-5-PENTYLBENZENE-L,3-DIOL

(71) Applicant: ENANTIA, S.L., Barcelona (ES)

(72) Inventors: Alexander Christian Comely, Barcelona (ES); Nicolas Tesson, Barcelona (ES); Carmen Jiménez González, Barcelona (ES)

(73) Assignee: ENANTIA, S.L., Barcelona (ES)

( * ) Notice: Subject to any disclaimer, the term of this patent is extended or adjusted under 35 U.S.C. 154(b) by 0 days.

(21) Appl. No.: 16/636,888

(22) PCT Filed: Aug. 6, 2018

(86) PCT No.: PCT/EP2018/071238
§ 371 (c)(1),
(2) Date: Feb. 5, 2020

(87) PCT Pub. No.: WO2019/030158
PCT Pub. Date: Feb. 14, 2019

(65) Prior Publication Data
US 2020/0369586 A1     Nov. 26, 2020

(30) Foreign Application Priority Data
Aug. 7, 2017   (EP) .................... 17382555

(51) Int. Cl.
| | | |
|---|---|---|
| C07C 39/17 | (2006.01) | |
| C07C 37/84 | (2006.01) | |
| C07C 229/12 | (2006.01) | |
| C07C 229/22 | (2006.01) | |
| C07D 209/42 | (2006.01) | |

(52) U.S. Cl.
CPC .............. *C07C 39/17* (2013.01); *C07C 37/84* (2013.01); *C07C 229/12* (2013.01); *C07C 229/22* (2013.01); *C07D 209/42* (2013.01); *C07B 2200/13* (2013.01)

(58) Field of Classification Search
None
See application file for complete search history.

(56) References Cited

U.S. PATENT DOCUMENTS 10,226,442 B2 * 3/2019 Tsai .............. A23L 33/16

FOREIGN PATENT DOCUMENTS

| EP | 2123626 A1 | 11/2009 |
|---|---|---|
| GB | 2393182 A | 3/2004 |
| WO | WO 2006/133941 A2 | 12/2006 |
| WO | WO 2007/041167 A2 | 4/2007 |
| WO | WO 2009/018389 A1 | 2/2009 |
| WO | WO 2015/032519 A1 | 3/2015 |
| WO | WO 2019/118360 A1 | 6/2019 |

OTHER PUBLICATIONS

Baek, et al: "Boron triflouride etherate on alimina—a modified Lewis acid reagent. An improved synthesis of cannabidiol", Tetrahedron Letters 1985, vol. 26, No. 8, pp. 1083-1086.
Jones, et al : "Cannabidiol", Acta Crystallographica 1977, Section B33, pp. 3211-3214. https://doi.org/10.1107/S0567740877010577.
Petrzilka, et al: "Synthese und chiralität des (−)-Cannabidiols vorläufige mitteilung", Helvetica Chimica Acta 1967, vol. 50, No. 2, pp. 719-723. https://doi.org/10.1002/hlca.19670500235.
Petrzilka, et al: "Synthese von haschisch-inhaltsstoffen. 4. Mitteilung", Helvetica Chimica Acta 1969, vol. 52, No. 4, pp. 1102-1134. https://doi.org/10.1002/hlca.19690520427.
ICH Topic Q1A(R2) Stability Testing of New Drug Substances and Products—Step 5 Note for Guidance on Stability Testing of New Drug Substances and Products, European Medicines Agency, Aug. 2003, CPMP/ICH/2736/99, available on the website http://www.ich.org/products/guidelines/quality/quality-single/article/stability-testing-of-new-drug-substances-and-products.html on Aug. 4, 2017.
Tilborg, et al: "Pharmaceutical salts and cocrystals involving amino acids: A brief structural overview of the state-of-art", European Journal of Medicinal Chemistry, Jan. 18, 2014, vol. 74, No. 18, pp. 411-426.
International Search Report and Written Opinion dated Oct. 18, 2018 for PCT Application No. PCT/EP2018/071238, 13 pages.
Shan, et al: "Impact of pharmaceutical cocrystals: the effects on drug pharmacokinetics", Aug. 4, 2014; Expert Opinion on Drug Metabolism & Toxicology, vol. 10, No. 9, pp. 1255-1271, XP-055513820.

* cited by examiner

*Primary Examiner* — Brian J Davis
(74) *Attorney, Agent, or Firm* — Squire Patton Boggs (US) LLP

(57) ABSTRACT

The present invention relates to cocrystals of 2-[(1R,6R)-6-isopropenyl-3-methylcyclohex-2-en-1-yl]-5-pentylbenzene-1,3-diol and a zwitterion coformer, processes for their preparation, and their use as a medicament and for the purification of 2-[(1R,6R)-6-isopropenyl-3-methylcyclohex-2-en-1-yl]-5-pentylbenzene-1,3-diol. The invention also relates to compositions comprising the cocrystal.

20 Claims, 13 Drawing Sheets

COCRYSTAL OF 2-[(1R,6R)-6-ISOPROPENYL-3-METHYLCYCLOHEX-2-EN-1-YL]-5-PENTYLBENZENE-L,3-DIOL

This application is a National Stage Application of International Application No. PCT/EP2018/071238 filed 6 Aug. 2018 which claims the benefit of EP application 17382555.5, filed on 7 Aug. 2017. EP application 17382555.5 is incorporated herein by reference in its entirety.

This application claims the benefit of European Patent Application EP17382555.5 filed on 7 Aug. 2017.

The present invention relates to cocrystals of 2-[(1R,6R)-6-isopropenyl-3-methylcyclohex-2-en-1-yl]-5-pentylbenzene-1,3-diol and a zwitterion coformer, processes for their preparation, and their use as a medicament or for the purification of 2-[(1R,6R)-6-isopropenyl-3-methylcyclohex-2-en-1-yl]-5-pentylbenzene-1,3-diol. It also relates to compositions comprising them.

BACKGROUND ART

Cannabidiol (abbreviated as (–)-CBD or CBD)) is the International Nonpropietary Name of 2-[(1R,6R)-6-isopropenyl-3-methylcyclohex-2-en-1-yl]-5-pentylbenzene-1,3-diol having the CAS number 13956-29-1. The structure of Cannabidiol corresponds to the formula (I):

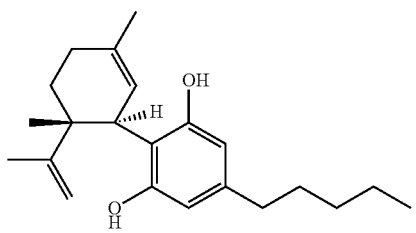

(I)

Cannabidiol is one of at least 113 active cannabinoids identified in cannabis. In particular, CBD is specially interesting because it has a pharmacologically broad spectrum activity without having undesirable psychotropic effects. CBD has a very low toxicity and very few adverse effects, and thus it is safe and well tolerated in humans. In particular, CBD is reported to have anti-inflammatory, antipsychotic and anticonvulsant activity and it is commercially available in the form of oral dosage forms such as oil, capsules or sublingual spray. CBD has the status of orphan drug for the treatment of Dravet syndrome, perinatal asphyxia and also for the prophylaxis of graft-vs-host disease.

Furthermore, researchers are currently investigating CBD for the prophylaxis and/or treatment of epilepsy, Parkinson's disease, Huntingdon's disease, spinal cord injury, stroke, cerebrovascular disorders, rheumatism, osteoporosis, arthritis, neuropathic pain, fibromyalgia, anxiety, post-traumatic stress disorder, depression, mood disorders, schizophrenia, nausea, motion sickness, multiple sclerosis, sleep disorders, eating disorders, cancers, metabolic syndrome, diabetes, obesity, liver disease, kidney disease, heart disease, glaucoma, colitis, irritable bowel syndrome, Crohn's disease, asthma, acne, psoriasis, pruritus and skin disorders.

However, its oral bioavailability is low (ranging from 6-33% in humans) due to its low aqueous solubility (about 0.1 ug/mL) and an extensive first-pass metabolism. In particular, CBD is insoluble in water but soluble in organic solvents such as pentane. Besides, CBD has a low melting point of 66° C. and is a colorless crystalline solid at room temperature. Unfortunately, due to its low melting point, potential localized melting of CBD during high energy process steps (such as milling, compression, and coating) presents a significant risk for the chemical stability of CBD during pharmaceutical formulation.

Furthermore, several degradation studies indicate that CBD is sensitive to commonly used synthetic reaction and storage conditions. In particular, it is known that under strongly basic media and in the presence of air, CBD is oxidized; and that under acidic conditions CBD is cyclized to obtain the undesirable by-product tetrahydrocannabinol (THC) which has undesirable psychotropic effects. Finally, it is also disclosed in the state of the art that CBD is photoreactive which means that it should be guarded from light when stored.

In order to overcome the very low solubility of CDB, complexes with cyclodextrine or maltodextrine suitable for sublingual administration have been disclosed in the state of the art. These complexes have been obtained by evaporation to dryness or by co-precipitation followed by freeze-drying, which means that these complexes are not in a crystalline form hindering the preparation of pharmaceutical dosage forms containing CBD.

The different solid forms of a pharmaceutically active ingredient can have different characteristics, and offer certain advantages, for example with regard to stability, bioavailability, ease of formulation, ease of administration, among others. Since some solid forms are more adequate for one type of formulation, and other forms for other different formulations, the development of new solid forms allows for improving the characteristics of the pharmaceutical formulations comprising them. In addition, depending on the therapeutic indications, one or another pharmaceutical formulation may be preferred.

Especially desirable improvements/advantages of the new crystalline form would include, for example, better stability, flowability, solubility, tractability, or compressibility, improvement of physicochemical properties in order to facilitate its manufacture or its formulation, to enhance the absorption and/or the bioavailability, being easily obtainable with more constant physicochemical properties, allowing more flexibility while formulating, or facilitating its formulation, better dispersibility properties, thus allowing better dispersion rates, especially if dispersed in an aqueous physiological medium, or reducing hygroscopicity, allowing new routes of administration.

Therefore, from what it is known in the state of the art, there is the need to find new CBD crystalline forms with improved physicochemical properties.

CBD is commonly obtained by several processes either by synthetic routes or by extraction processes from plants such as those of the genus *Cannabis* (such as *Cannabis* indica and *Cannabis sativa*). Particularly, CBD extraction processes typically involve one or more extraction steps from the *Cannabis* plant; followed by decarboxylation steps to transform the acid form of cannabinoids (such as tetrahydrocannabinolic acid (THCA) and cannabidiolic acid (CBDA)) into neutral cannabinoids (such as THC and CBD); and finally one or more purification steps. This purification process comprises evaporation steps (to remove volatile impurity); winterization procedures (to remove wax impurity); filtration through silica plug (to remove highly polar impurities); column chromatography, crystallisation and high vacuum (to remove residual solvent). However, combinations of these processes are laborious, time consuming, not economical and can lead to CBD in a low yield.

Several synthetic processes have been disclosed in the state of the art. In particular, these synthetic processes are based on acid-catalysed terpenylation of phenols, for example the acid-catalyzed condensation of (+)-p-mentha-2,8-dien-1-ol with olivetol. The reaction conditions of these reaction involve the use of N,N-dimethylformamide dineopentyl acetal (cf. T. Petrzilka et al. "synthese und chiralität des (−)-cannabidiols vorlsufige mitteilung". Helvetica Chimica Acta. 1967, vol. 50(2), pp. 719-23); picric acid, oxalic acid or maleic acid (cf. T. Petrzilka et al. "synthese von haschisch-inhaltsstoffen. 4. Mitteilung". Helvetica Chimica Acta. 1969, vol. 52(4), pp. 1102-34); p-toluensulfonic acid (PTSA) (cf. PCT patent application WO2009018389); $BF_3$-$Et_2O$/alumina (cf. Tetrahedron Letters 1985, 26(8), 1083); or $ZnCl_2$ (cf. PCT patent application WO2006133941). However, these processes give CBD in low yield and with a considerable number of undesirable by-products (including THC). Moreover, these processes also comprise complicated purification steps. In particular, the purification/isolation steps comprise the use of column chromatography techniques or the use of a combination of fractional distillation and crystallization of CBD from organic solvent media.

In order to increase the purity of CBD, the use of the above mentioned acid-catalysed terpenylations of phenols has been disclosed using an ester of olivetolic acid as starting material instead of olivetol (cf. PCT patent applications WO2007041167 and WO2015032519). In these processes, an additional decarboxylation step is at least necessary to obtain pure CBD. However, the ester of olivetolic acid is very expensive and its use hinders the cost-effectiveness of this route.

Therefore, from what is known in the state of the art, there is still the need for a robust CBD purification process affording high purity and high yield.

SUMMARY OF INVENTION

The inventors provide cocrystals of CBD that overcome the problems associated with the preparation of CBD with a high purity mentioned in the state of the art and their use as a medicament. The inventors have found that the cocrystals of the present invention allow for purifying CBD with a simple, cost-effective and industrial scalable process.

In particular, the cocrystals of the present invention allow for purifying CBD both when CBD is obtained by a plant extraction process and when obtained from synthetic routes. As shown in the Examples, the cocrystals of the present invention allow for purifying the CBD when the starting CBD already has high purity (about 98% a/a) and even when the CBD used as starting material is a plant extract with low purity (about 50% w/w) to provide CBD of purity higher than 99%.

Thus, the use of the cocrystals of the present invention allows for compliance with the strict criteria of impurities limit specifications required by the medicine regulatory agencies. They can also be used as intermediates useful for the purification of CBD.

Furthermore, the cocrystal of the present invention has a higher melting point than CBD. This is advantageous because the increase in the melting point allows for reducing the potential amorphization due to localized melting of the active ingredient during the storage or during the preparation of the final dosage form. Therefore, as shown in the Examples, the cocrystals of the present invention, more in particular the cocrystal of 2-[(1R,6R)-6-isopropenyl-3-methylcyclohex-2-en-1-yl]-5-pentylbenzene-1,3-diol with L-proline (cocrystal Form I), have a good stability making them suitable for use as a medicament.

Accordingly, the provision of a cocrystal of CBD having improved properties is considered a contribution to the art. Thus, a first aspect of the invention relates to a cocrystal of 2-[(1R,6R)-6-isopropenyl-3-methylcyclohex-2-en-1-yl]-5-pentylbenzene-1,3-diol (CBD) and a zwitterion coformer.

A second aspect of the invention relates to a process for the preparation of the cocrystal as defined in the first aspect of the invention, which comprises: (a) wet grinding a mixture of CBD and the co-former in a solvent; and (b) drying the cocrystal thus obtained; or alternatively (c) slurrying the CBD with a coformer and an organic solvent; and (d) isolating the cocrystal thus obtained.

The third aspect of the invention relates to a process for the purification of CBD which comprises (e) dissociating a cocrystal as defined in the first aspect of the invention under such reaction conditions to obtain CBD; and (f) isolating CBD thus obtained.

A fourth aspect of the invention relates to a pharmaceutical composition comprising a pharmaceutically effective amount of the cocrystal of CBD and a "pharmaceutically acceptable coformer" as defined in the first aspect of the invention together with one or more appropriate acceptable excipients or carriers.

Finally, a fifth aspect of the invention relates to a cocrystal of CBD and a coformer as defined in the first aspect of the invention for use as a medicament.

DETAILED DESCRIPTION OF THE INVENTION

Figure 1:
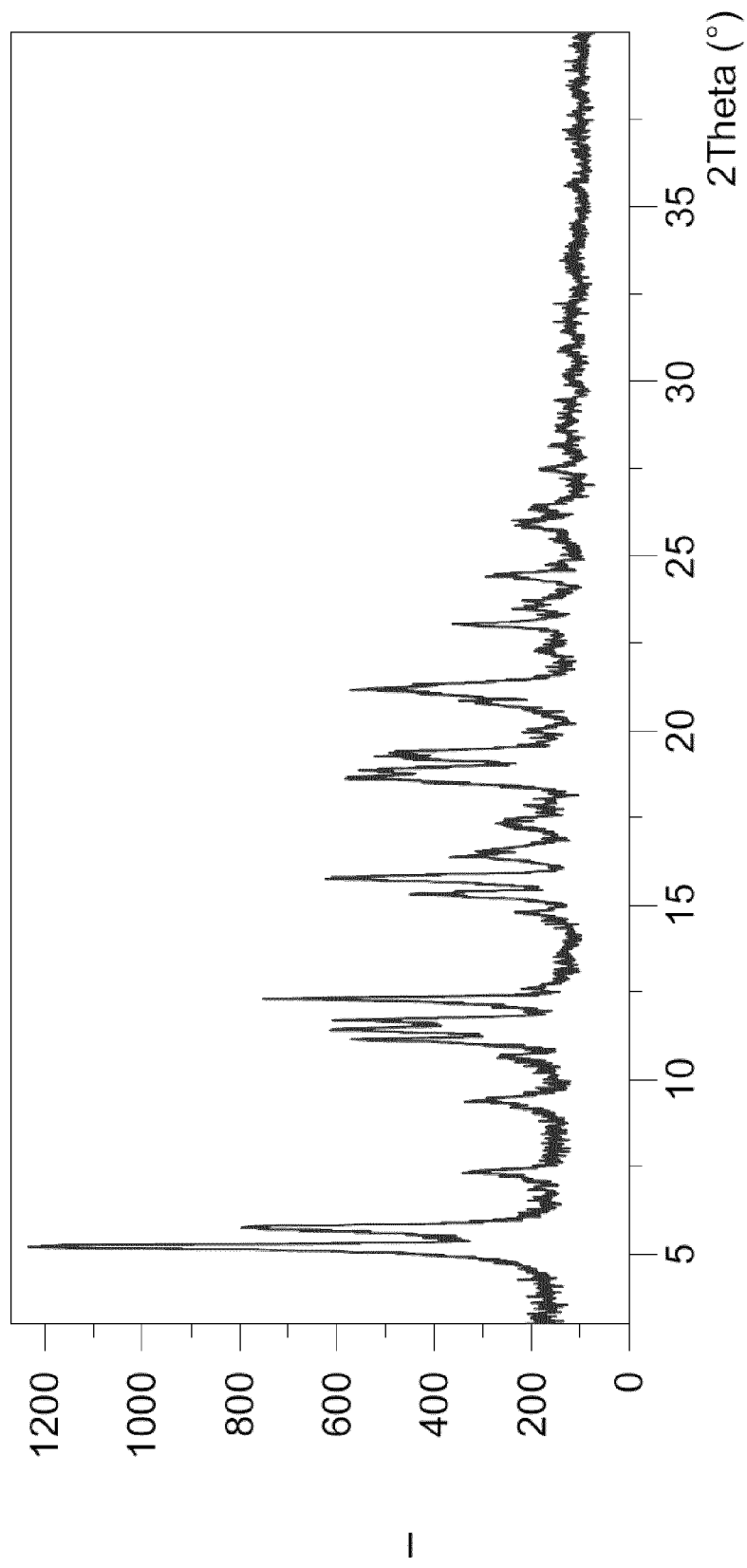
FIG. 1 shows the X-ray powder diffractogram (XRPD) of the cocrystal Form I. The spectrum expresses intensity (I; counts) versus degrees 2 theta (°).

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper end-points of the range. Ranges and values given, such as temperatures, times, and the like, should be considered approximate, unless specifically stated.

For the purposes of the invention, the term "cocrystal" refers herein to a crystalline entity with at least two different components (also named "coformers") constituting the unit cell at room temperature (20-25° C.) and interacting by weak interactions. Thus, in a cocrystal, one component crystallizes with one or more neutral components. The cocrystals may include one or more solvent molecules in the crystal lattice.

When values of characteristic peaks of an X-ray diffractogram are given it is said that these are "approximate" values. It should be understood that the values are the ones shown in the corresponding lists or tables ±0.3 degrees 2 theta measured in an X-ray diffractometer with Cu—K$_\alpha$ radiation λ=1.5406 Å.

The terms "wet grinding" and "liquid assisted grinding" are equivalent and refer to a technique which consists of milling or grinding the product or mixture with some drops of solvent added. Neat and liquid-assisted grinding are techniques that can be employed in order to produce cocrystals. In neat (dry) grinding, cocrystal formers are ground together manually using a mortar and pestle, using a ball mill, or using a vibratory mill. In liquid-assisted grinding, or kneading, a small or substoichiometric amount of liquid (solvent) is added to the grinding mixture.

The term "slurrying" as disclosed herein refers to any process which employs a solvent to wash or disperse by stirring a suspension of a compound.

The term "room temperature" refers to a temperature of the environment, without heating or cooling, and is generally comprised from 20° C. to 25° C.

The term "overnight" refers to a time interval comprised from 10 h to 20 h.

The term "molar ratio" has been used to express the stoichiometric amount in mols of a compound in relation to another compound. For example, the stoichiometric amount in mols of one of the coformers of the cocrystal in relation to the other coformer. The molar ratio can be determined by $^1$H NMR.

As mentioned above, the first aspect of the invention refers to cocrystals of CBD and a coformer.

In an embodiment, the coformer is a "pharmaceutically acceptable coformer". The term "pharmaceutically acceptable coformer" refers to a coformer suitable for use as a pharmaceutical agent in the preparation of compositions with medical use. It must also be suitable for use in contact with the tissue or organ of humans and animals without excessive toxicity, irritation, allergic response, immunogenicity or other problems or complications commensurate with a reasonable benefit/risk ratio.

In an embodiment, the coformer is a zwitterion. The term "zwitterion" refers to a molecule having separate and distinct positively and negatively charged moieties resident on the same molecule. In an embodiment, the zwitterion comprises a positively charged nitrogen group and a negatively charged group distal to the positively charged nitrogen group on the organic zwitterion such that there is a separation by at least one carbon atom; preferably from 2 to 3 carbon atoms. In an embodiment, the coformer is a zwitterion selected form the group consisting of L-proline, betaine, L-carnitine, D-proline, DL-proline and (2S,3aS,7aS)-octahydro-1H-indole-2-carboxylic acid. In an embodiment, the coformer is a zwitterion selected form the group consisting of L-proline, betaine and L-carnitine.

In an embodiment, the cocrystal of the invention is a cocrystal of CBD and L-proline, also named Form I. For the purposes of the invention, L-proline is the International Nonproprietary Name (INN) of (S)-pyrrolidinecarboxylic acid, and has the CAS No. 147-85-3. The structure of L-proline is the following:

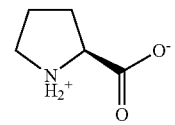

In an embodiment, the cocrystal Form I of the present invention is characterized by having an X-ray powder diffractogram that comprises characteristic peaks at 5.8, 11.1 and 15.8±0.3 degrees 2 theta at a Cu—K$_\alpha$ radiation, λ=1.5406 Å. In an embodiment, the cocrystal Form I of the present invention is characterized by having an X-ray powder diffractogram that comprises further characteristic peaks at 7.4, 11.4 and 21.2±0.3 degrees 2 theta at a Cu—K$_\alpha$ radiation, λ=1.5406 Å.

More specifically, the cocrystal Form I of the present invention is characterized by exhibiting in the X-ray powder diffractogram a pattern of peaks, expressed in 2 theta units in degrees, 2θ (°), which is shown in Table 1.

TABLE 1

List of selected peaks (only peaks with relative intensity greater than or equal to 1% are indicated):

| Pos. [°2θ] | d-spacing [Å] | Rel. Int. [%] |
|---|---|---|
| 5.3 | 16.8 | 100 |
| 5.8 | 15.3 | 63 |
| 7.4 | 12.0 | 17 |
| 9.4 | 9.4 | 16 |
| 10.6 | 8.3 | 10 |
| 11.1 | 7.9 | 40 |
| 11.4 | 7.7 | 44 |
| 11.7 | 7.6 | 40 |
| 12.3 | 7.2 | 61 |
| 14.8 | 6.0 | 9 |
| 15.3 | 5.8 | 26 |
| 15.8 | 5.6 | 42 |
| 16.4 | 5.4 | 18 |
| 17.4 | 5.1 | 10 |

TABLE 1-continued

List of selected peaks (only peaks with relative intensity greater than or equal to 1% are indicated):

| Pos. [°2θ] | d-spacing [Å] | Rel. Int. [%] |
|---|---|---|
| 18.6 | 4.8 | 41 |
| 18.9 | 4.7 | 37 |
| 19.4 | 4.6 | 32 |
| 20.0 | 4.4 | 6 |
| 21.2 | 4.2 | 38 |
| 22.3 | 4.0 | 3 |
| 23.0 | 3.9 | 21 |
| 23.5 | 3.8 | 8 |
| 24.5 | 3.6 | 14 |
| 25.9 | 3.4 | 10 |
| 26.4 | 3.4 | 8 |
| 27.5 | 3.2 | 6 |
| 29.0 | 3.1 | 1 |
| 30.1 | 3.0 | 2 |
| 35.6 | 2.5 | 2 |

The cocrystal Form I of the present invention may be further characterized by an X-ray diffractogram as in FIG. 1.

The cocrystal Form I of the present invention may also be further characterized by the following $^1$H NMR spectrum (CD$_3$OD, 400 MHz, δ): 6.08 (s, 2H, ArH); 5.29 (s, 1H); 4.45 (d, 2H, J=14.4 Hz); 3.98-3.90 (m, 2H); 3.42-3.35 (m, 1H); 3.26-3.19 (m, 1H); 2.94-2.87 (m, 1H); 2.38 (t, 2H, J=7.2 Hz); 2.34-2.25 (m, 1H); 2.24-2.08 (m, 2H); 2.04-1.91 (m, 3H); 1.76-1.71 (m, 2H); 1.68 (s, 3H); 1.64 (s, 3H); 1.58-1.51 (m, 2H); 1.39-1.24 (m, 4H); 0.90 (t, 3H, J=7.2 Hz).

Figure 11:
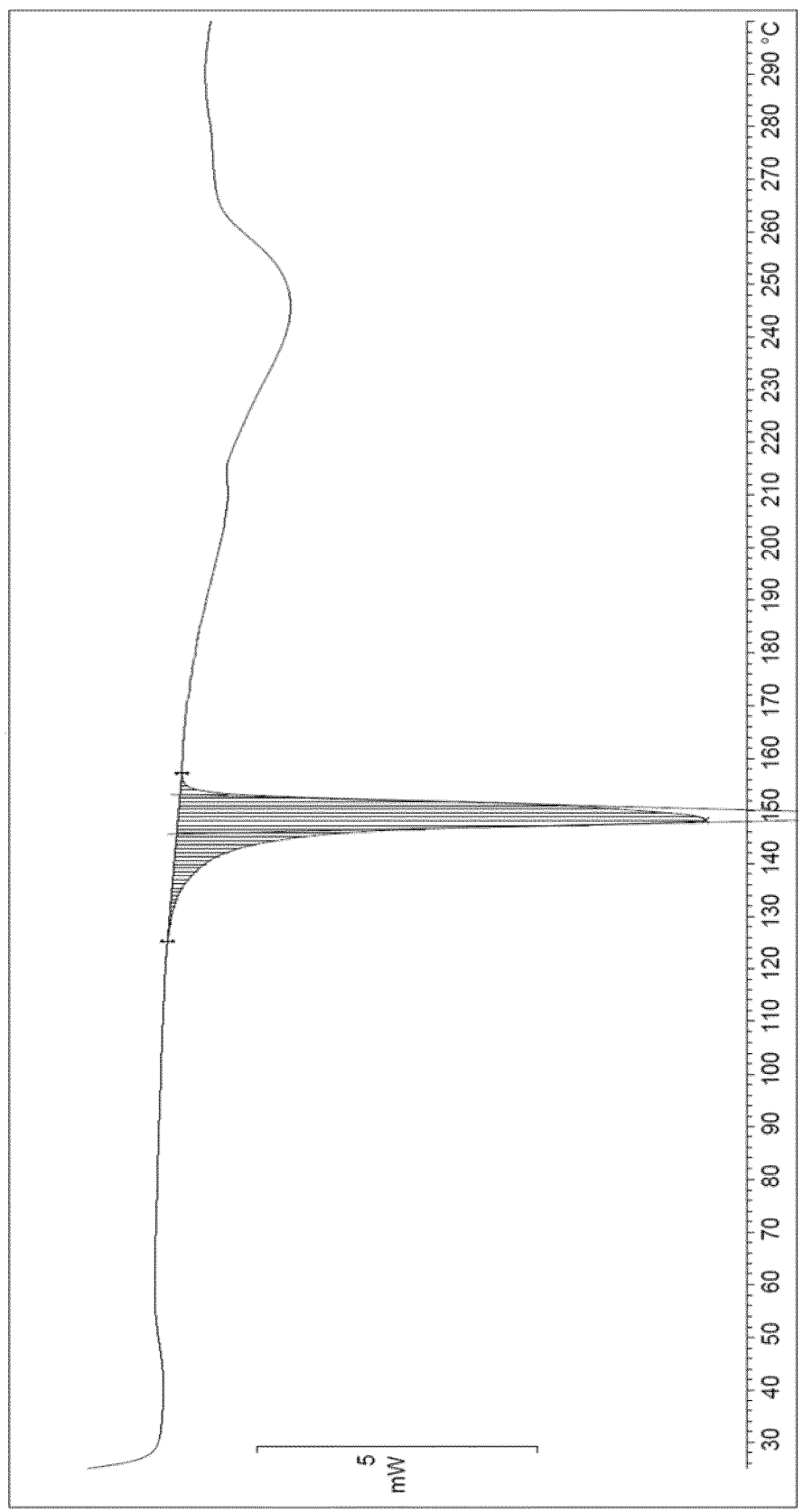
FIG. 11 shows the DSC of cocrystal Form I. The spectrum expresses the heat flow (mW/mg) versus temperature (C).

The cocrystal Form I of the present invention may also be further characterized by DSC (differential scanning calorimetry) analysis as shown in FIG. 11. The DSC analysis of cocrystal Form I shows an endothermic event with an onset at 145.3° C. which corresponds to the melting point of cocrystal Form I followed by endothermic peaks possibly due to degradation (decomposition) events. The cocrystal Form I of the present invention may also be further characterized by having a melting range of 142-152° C.

The cocrystal Form I of the present invention may also be further characterized by thermogravimetric analysis (TGA). The TG analysis of cocrystal Form I shows a weight loss between 26.7° C. and 61.5° C. that corresponds to the loss of about 0.05 water molecule (0.20%, where the calculated value corresponding to one water molecule is 4.0%). Therefore, TGA confirms that cocrystal Form I of the present invention is not a hydrate. The TGA of cocrystal Form I shows no significant weight loss before its melting (cf. FIG. 2).

The cocrystal of Form I of the present invention prepared from pure commercial CBD (98.8% a/a HPLC) has a purity equal to or higher than 99% a/a measured by HPLC. It is worth noting that the coformer is not detected in the HPLC conditions used in this analysis.

The cocrystal Form I of the present invention is in a molar ratio 1:1 (CBD:L-proline).

In an embodiment, the cocrystal of the invention is a cocrystal of CBD and betaine, also named Form II. For the purposes of the invention, betaine is the International Nonproprietary Name (INN) of 2-trimethylammonioacetate, and has the CAS No. 107-43-7. The structure of betaine is the following:

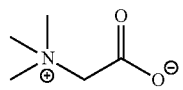

In an embodiment, the cocrystal Form II of the present invention is characterized by having an X-ray powder diffractogram that comprises characteristic peaks at 9.1, 10.7 and 18.4±0.3 degrees 2 theta at a Cu—K$_\alpha$ radiation, λ=1.5406 Å. In an embodiment, the cocrystal Form II of the present invention is characterized by having an X-ray powder diffractogram that comprises further characteristic peaks at 5.3 and 13.0±0.3 degrees 2 theta at a Cu—K$_\alpha$ radiation, λ=1.5406 Å.

More specifically, the cocrystal Form II of the present invention is characterized by exhibiting in the X-ray powder diffractogram a pattern of peaks, expressed in 2 theta units in degrees, 2θ (°), which is shown in Table 2.

TABLE 2

List of selected peaks (only peaks with relative intensity greater than or equal to 1% are indicated):

| Pos. [°2θ] | d-spacing [Å] | Rel. Int. [%] |
|---|---|---|
| 5.3 | 16.6 | 100 |
| 9.1 | 9.7 | 46 |
| 10.7 | 8.3 | 11 |
| 12.0 | 7.4 | 4 |
| 12.4 | 7.2 | 5 |
| 13.0 | 6.8 | 69 |
| 14.0 | 6.3 | 6 |
| 14.4 | 6.1 | 7 |
| 15.2 | 5.8 | 13 |
| 16.1 | 5.5 | 4 |
| 16.6 | 5.3 | 38 |
| 16.9 | 5.3 | 12 |
| 17.1 | 5.2 | 7 |
| 17.7 | 5.0 | 18 |
| 18.4 | 4.8 | 77 |
| 19.0 | 4.7 | 5 |
| 20.0 | 4.4 | 6 |
| 20.5 | 4.3 | 1 |
| 21.0 | 4.2 | 13 |
| 21.6 | 4.1 | 19 |
| 21.9 | 4.0 | 6 |
| 23.5 | 3.8 | 6 |
| 23.8 | 3.7 | 10 |
| 24.5 | 3.6 | 6 |
| 25.6 | 3.5 | 4 |
| 26.2 | 3.4 | 5 |
| 26.8 | 3.3 | 3 |
| 27.7 | 3.2 | 5 |

Figure 3:
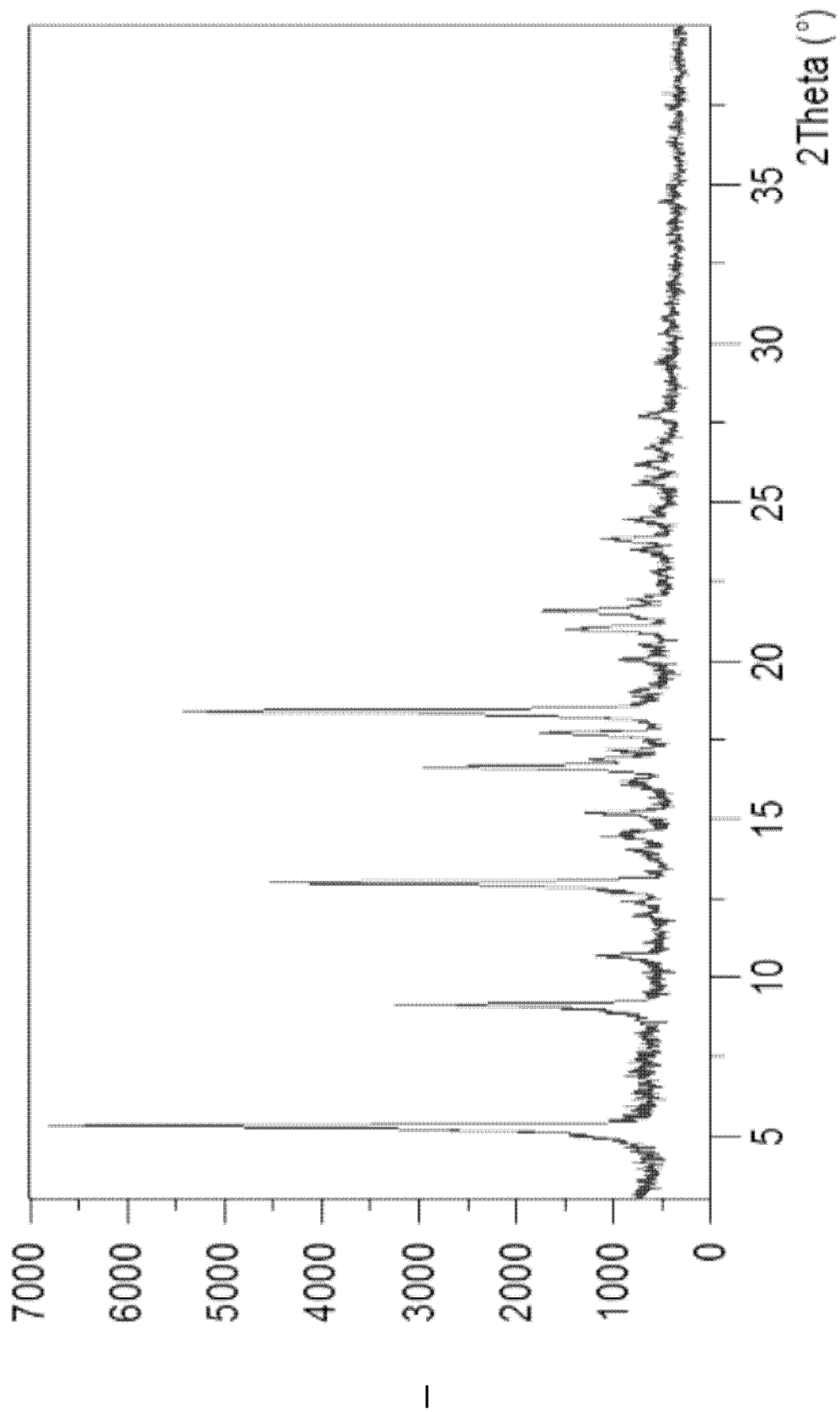
FIG. 3 shows the X-ray powder diffractogram (XRPD) of the cocrystal Form II. The spectrum expresses intensity (I; counts) versus degrees 2 theta (°).

The cocrystal Form II of the present invention may be further characterized by an X-ray diffractogram as in FIG. 3.

The cocrystal Form II of the present invention may also be further characterized by the following $^1$H NMR spectrum (CD$_3$OD, 400 MHz, δ): 6.08 (s, 2H, ArH); 5.29 (s, 1H); 4.47-4.43 (m, 2H); 3.95-3.90 (m, 1H); 3.62 (s, 2H); 3.27 (s, 9H); 2.94-2.86 (m, 1H); 2.38 (t, 2H, J=7.2 Hz); 2.25-2.15 (m, 1H); 2.04-1.96 (m, 1H); 1.76-1.71 (m, 2H); 1.68 (s, 3H); 1.64 (s, 3H); 1.59-1.51 (m, 2H); 1.38-1.24 (m, 4H); 0.90 (t, 3H, J=7.2 Hz).

The cocrystal Form II of the present invention may also be further characterized by DSC (differential scanning calorimetry) analysis. The DSC analysis of cocrystal Form II shows endothermic events with an onset at 32.0° C., 79.2° C., 159.0° C. and 233.0° C.

The cocrystal of Form II of the present invention prepared from pure commercial CBD (98.8% a/a HPLC) has a purity equal to or higher than 99% a/a measured by HPLC. It is worth noting that the coformer is not detected in the HPLC conditions used in this analysis.

The cocrystal Form II of the present invention is in a molar ratio 1:1 (CBD:betaine).

In an embodiment, the cocrystal of the invention is a cocrystal of CBD and L-carnitine, also named Form III. For the purposes of the invention, L-carnitine is the International Nonproprietary Name (INN) of (3R)-3-hydroxy-4-(trimethylammonio)butanoate, and has the CAS No. 541-15-1. The structure of L-carnitine is the following:

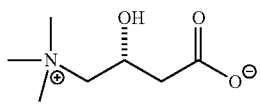

In an embodiment, the cocrystal Form III of the present invention is characterized by having an X-ray powder diffractogram that comprises characteristic peaks at 6.8, 11.3 and 20.0±0.3 degrees 2 theta at a Cu—K$_\alpha$ radiation, $\lambda$=1.5406 Å. In an embodiment, the cocrystal Form III of the present invention is characterized by having an X-ray powder diffractogram that comprises further characteristic peaks at 12.7, 13.6, and 15.6±0.3 degrees 2 theta at a Cu—K$_\alpha$ radiation, $\lambda$=1.5406 Å.

More specifically, the cocrystal Form III of the present invention is characterized by exhibiting in the X-ray powder diffractogram a pattern of peaks, expressed in 2 theta units in degrees, 2θ (°), which is shown in Table 3.

TABLE 3

List of selected peaks (only peaks with relative intensity greater than or equal to 1% are indicated):

| Pos. [°2θ] | d-spacing [Å] | Rel. Int. [%] |
|---|---|---|
| 6.8 | 13.0 | 100 |
| 8.8 | 10.1 | 26 |
| 10.2 | 8.7 | 15 |
| 11.3 | 7.9 | 44 |
| 11.6 | 7.6 | 22 |
| 11.9 | 7.4 | 11 |
| 12.7 | 7.0 | 17 |
| 13.6 | 6.5 | 33 |
| 13.9 | 6.4 | 34 |
| 14.9 | 6.0 | 5 |
| 15.6 | 5.7 | 35 |
| 16.2 | 5.5 | 70 |
| 17.0 | 5.2 | 13 |
| 17.7 | 5.0 | 29 |
| 17.9 | 5.0 | 18 |
| 19.5 | 4.5 | 30 |
| 20.0 | 4.4 | 42 |
| 21.0 | 4.2 | 51 |
| 22.2 | 4.0 | 33 |
| 22.7 | 3.9 | 11 |
| 24.5 | 3.6 | 26 |
| 28.3 | 3.2 | 5 |
| 28.3 | 3.1 | 7 |
| 29.4 | 3.0 | 7 |
| 30.0 | 3.0 | 6 |

Figure 4:
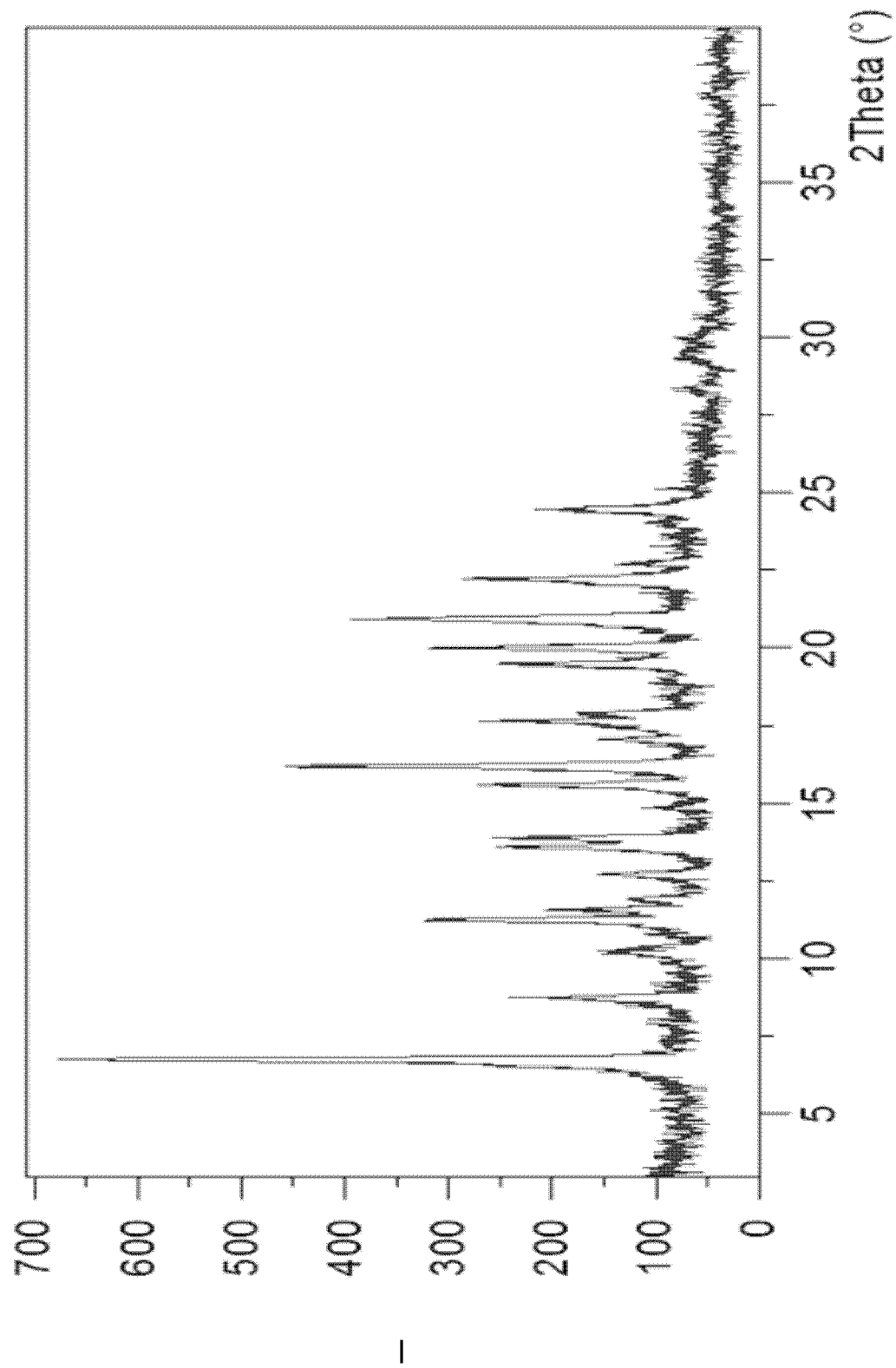
FIG. 4 shows the X-ray powder diffractogram (XRPD) of the cocrystal Form III. The spectrum expresses intensity (I; counts) versus degrees 2 theta (°).

The cocrystal Form III of the present invention may be further characterized by an X-ray diffractogram as in FIG. 4.

The cocrystal Form III of the present invention may also be further characterized by the following $^1$H NMR spectrum (CD$_3$OD, 400 MHz, δ): 6.08 (s, 2H, ArH); 5.29 (s, 1H); 4.48-4.42 (m, 4H); 3.95-3.90 (m, 1H); 3.42-3.33 (m, 4H); 3.22 (s, 18H); 2.94-2.88 (m, 1H); 2.40-2.16 (m, 7H); 2.04-1.95 (m, 1H); 1.76-1.71 (m, 2H); 1.68 (s, 3H); 1.64 (s, 3H); 1.58-1.51 (m, 2H); 1.39-1.24 (m, 4H); 0.90 (t, 3H, J=7.2 Hz).

The cocrystal Form III of the present invention may also be further characterized by DSC (differential scanning calorimetry) analysis. The DSC analysis of cocrystal Form III shows a first endothermic event with an onset at 56.4° C.; a second event with an onset at 112.7° C.; a third event having an onset at 138.7° C. and finally, an endothermic event with an onset at 174.7° C.

It was checked that the two first thermal events with an onset at 56.4 and 112.7° C. do not correspond to melting events. The solids obtained after both events correspond after rapid cooling to RT to Form III. Therefore, these events should correspond to water desorption and/or dehydration. In case of dehydration, the crystalline form could lead to a dehydrated form with a unit cell size identical to Form III or, it is possible that this dehydrated form converted into Form III before XRPD analysis. The third event with an onset at 138.7° C. corresponds to a solid-solid transformation of Form III to another crystal form. Therefore melting of cocrystal Form III was not observed.

The cocrystal of Form III of the present invention prepared from pure commercial CBD (98.9% a/a HPLC) has a purity similar to the starting material. It is worth noting that the coformer is not detected in the HPLC conditions used in this analysis.

The cocrystal Form III of the present invention is in a molar ratio 1:2 (CBD:L-carnitine).

In an embodiment, the cocrystal of the invention is a cocrystal of CBD and D-proline, also named Form IV. For the purposes of the invention, D-proline is the International Nonproprietary Name (INN) of (R)-pyrrolidinecarboxylic acid, and has the CAS No. 344-25-2. The structure of D-proline is the following:

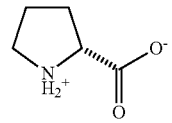

In an embodiment, the cocrystal Form IV of the present invention is characterized by having an X-ray powder diffractogram that comprises characteristic peaks at 5.7, 11.2 and 15.7±0.3 degrees 2 theta at a Cu—K$_\alpha$ radiation, $\lambda$=1.5406 Å. In an embodiment, the cocrystal Form IV of the present invention is characterized by having an X-ray powder diffractogram that comprises further characteristic peaks at 11.5 and 21.1±0.3 degrees 2 theta at a Cu—K$_\alpha$ radiation, $\lambda$=1.5406 Å.

More specifically, the cocrystal Form IV of the present invention is characterized by exhibiting in the X-ray powder diffractogram a pattern of peaks, expressed in 2 theta units in degrees, 2θ (°), which is shown in Table 5.

TABLE 5

List of selected peaks (only peaks with relative intensity greater than or equal to 1% are indicated):

| Pos. [°2θ] | d-spacing [Å] | Rel. Int. [%] |
|---|---|---|
| 5.2 | 17.0 | 100 |
| 5.7 | 15.4 | 99 |
| 9.4 | 9.4 | 24 |
| 10.3 | 8.6 | 6 |
| 10.6 | 8.3 | 11 |
| 11.2 | 7.9 | 35 |
| 11.5 | 7.7 | 58 |
| 12.4 | 7.1 | 40 |
| 12.7 | 7.0 | 11 |

TABLE 5-continued

List of selected peaks (only peaks with relative intensity greater than or equal to 1% are indicated):

| Pos. [°2θ] | d-spacing [Å] | Rel. Int. [%] |
|---|---|---|
| 13.7 | 6.5 | 1 |
| 14.7 | 6.0 | 8 |
| 15.3 | 5.8 | 19 |
| 15.7 | 5.6 | 39 |
| 16.3 | 5.4 | 28 |
| 17.3 | 5.1 | 27 |
| 18.6 | 4.8 | 45 |
| 19.2 | 4.6 | 18 |
| 19.4 | 4.6 | 15 |
| 20.2 | 4.4 | 8 |
| 20.7 | 4.3 | 20 |
| 21.1 | 4.2 | 34 |
| 22.2 | 4.0 | 5 |
| 22.7 | 3.9 | 2 |
| 23.2 | 3.8 | 17 |
| 23.9 | 3.7 | 6 |
| 24.6 | 3.6 | 9 |
| 25.6 | 3.5 | 6 |
| 26.2 | 3.4 | 10 |
| 27.6 | 3.2 | 3 |
| 28.3 | 3.2 | 2 |
| 31.3 | 2.9 | 3 |
| 32.1 | 2.8 | 1 |
| 33.1 | 2.7 | 2 |
| 33.9 | 2.6 | 3 |

Figure 7:
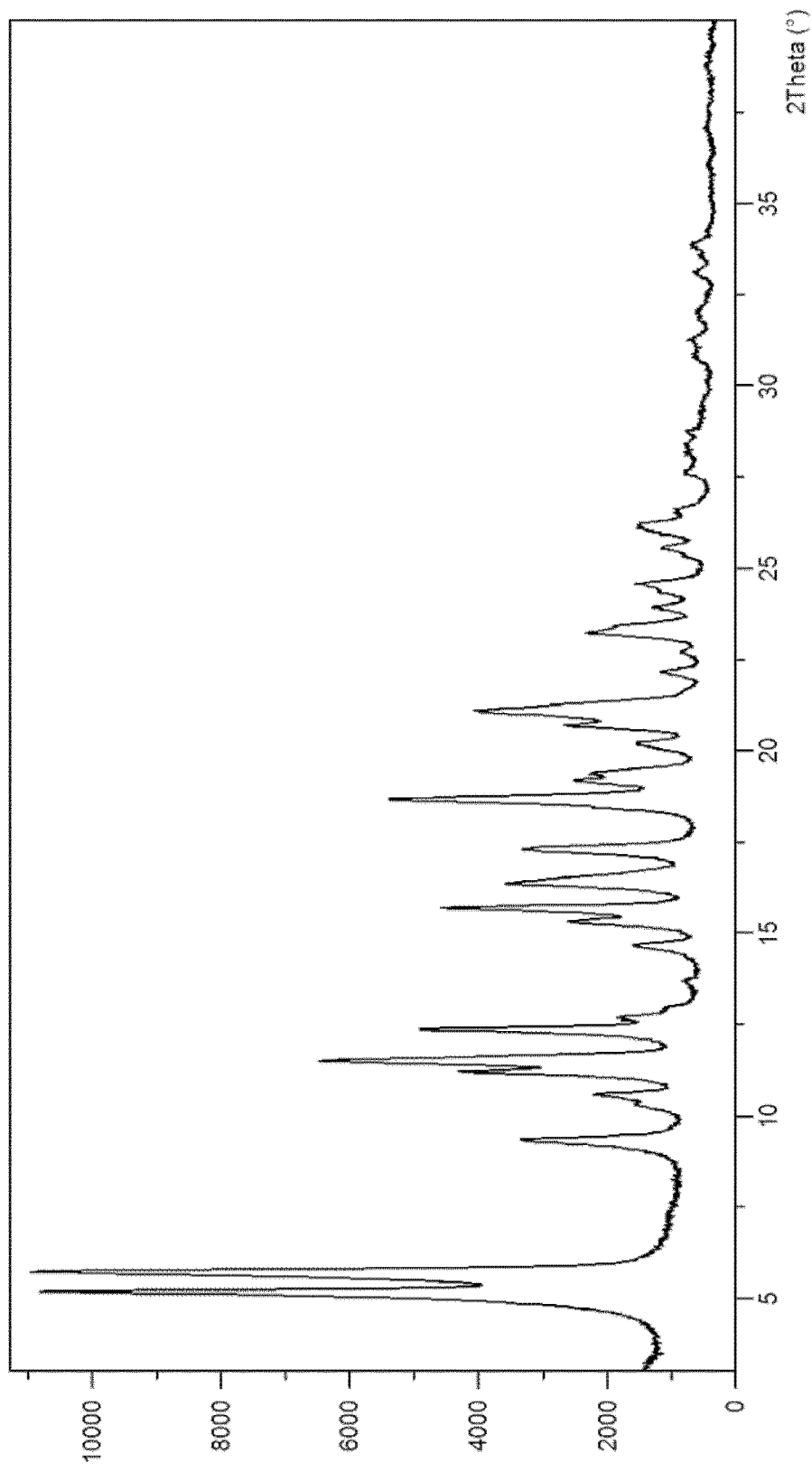
FIG. 7 shows the X-ray powder diffractogram (XRPD) of the cocrystal Form IV. The spectrum expresses intensity (I; counts) versus degrees 2 theta (°).

The cocrystal Form IV of the present invention may be further characterized by an X-ray diffractogram as in FIG. 7.

The cocrystal Form IV of the present invention may also be further characterized by the following $^1$H NMR spectrum (CD$_3$OD, 400 MHz, δ): 6.08 (s, 2H, ArH); 5.29 (s, 1H); 4.45 (d, 2H, J=14.2 Hz); 3.99-3.90 (m, 2H); 3.42-3.35 (m, 1H); 3.26-3.20 (m, 1H); 2.94-2.86 (m, 1H); 2.38 (t, 2H, J=7.7 Hz); 2.35-2.25 (m, 1H); 2.24-2.08 (m, 2H); 2.02-1.92 (m, 3H); 1.77-1.71 (m, 2H); 1.68 (s, 3H); 1.64 (s, 3H); 1.59-1.51 (m, 2H); 1.39-1.25 (m, 4H); 0.90 (t, 3H, J=7.0 Hz).

Figure 8:
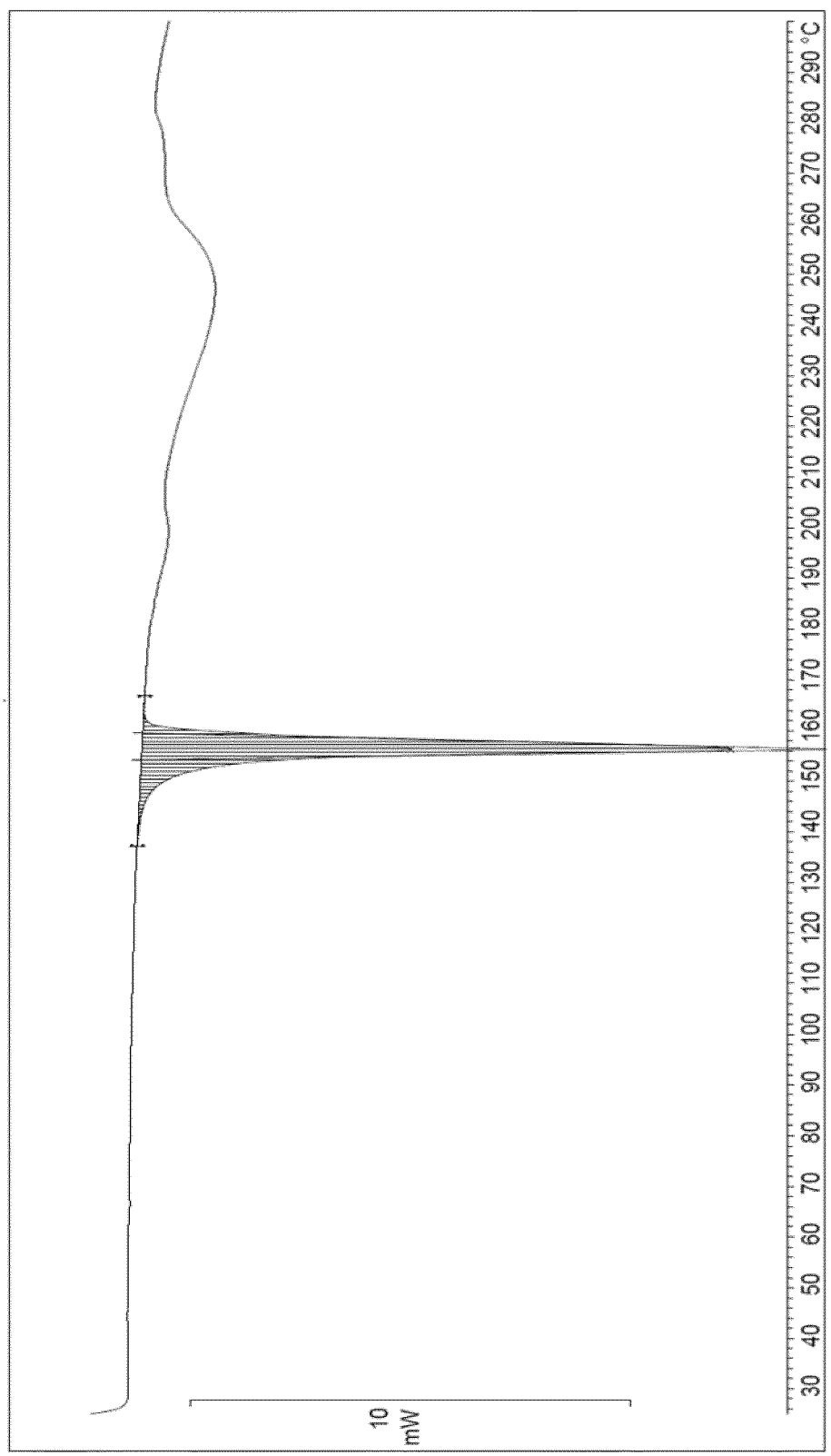
FIG. 8 shows the DSC of cocrystal Form IV. The spectrum expresses the heat flow (mW/mg) versus temperature (C).

The cocrystal Form IV of the present invention may also be further characterized by DSC (differential scanning calorimetry) analysis as shown in FIG. 8. The DSC analysis of cocrystal Form IV shows an endothermic event with an onset at 154.0° C. which corresponds to the melting point of cocrystal Form IV followed by endothermic peaks possibly due to degradation (decomposition) events. The cocrystal Form IV of the present invention may also be further characterized by having a melting range of 152-160° C.

The cocrystal of Form IV of the present invention prepared from pure commercial CBD (98.6% a/a HPLC) has a purity similar to the starting material. It is worth noting that the coformer is not detected in the HPLC conditions used in this analysis.

The cocrystal Form IV of the present invention is in a molar ratio 1:1 (CBD:D-proline).

In an embodiment, the cocrystal of the invention is a cocrystal of CBD and DL-proline, also named Form V. For the purposes of the invention, DL-proline is the International Nonproprietary Name (INN) of (rac)-pyrrolidinecarboxylic acid, and has the CAS No. 609-36-9. The structure of DL-proline is the following:

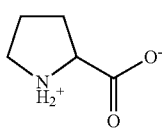

In an embodiment, the cocrystal Form V of the present invention is characterized by having an X-ray powder diffractogram that comprises characteristic peaks at 5.7, 11.1 and 15.7±0.3 degrees 2 theta at a Cu—K$_\alpha$ radiation, λ=1.5406 Å. In an embodiment, the cocrystal Form V of the present invention is characterized by having an X-ray powder diffractogram that comprises further characteristic peaks at 11.4 and 21.0±0.3 degrees 2 theta at a Cu—K$_\alpha$ radiation, λ=1.5406 Å.

More specifically, the cocrystal Form V of the present invention is characterized by exhibiting in the X-ray powder diffractogram a pattern of peaks, expressed in 2 theta units in degrees, 2θ (°), which is shown in Table 6.

TABLE 6

List of selected peaks (only peaks with relative intensity greater than or equal to 1% are indicated):

| Pos. [°2θ] | d-spacing [Å] | Rel. Int. [%] |
|---|---|---|
| 5.2 | 17.1 | 100 |
| 5.7 | 15.5 | 97 |
| 9.4 | 9.5 | 27 |
| 10.6 | 8.4 | 15 |
| 11.1 | 7.9 | 32 |
| 11.4 | 7.7 | 53 |
| 12.3 | 7.2 | 37 |
| 12.6 | 7.0 | 8 |
| 13.6 | 6.5 | 2 |
| 14.7 | 6.0 | 8 |
| 15.3 | 5.8 | 19 |
| 15.7 | 5.6 | 46 |
| 16.3 | 5.4 | 24 |
| 17.3 | 5.1 | 21 |
| 18.6 | 4.8 | 41 |
| 19.1 | 4.6 | 21 |
| 20.1 | 4.4 | 5 |
| 20.7 | 4.3 | 18 |
| 21.0 | 4.2 | 37 |
| 22.2 | 4.0 | 4 |
| 23.1 | 3.8 | 11 |
| 24.4 | 3.7 | 8 |
| 25.5 | 3.5 | 3 |
| 25.9 | 3.4 | 6 |
| 27.5 | 3.2 | 2 |
| 28.5 | 3.1 | 1 |
| 30.8 | 2.9 | 1 |
| 32.0 | 2.8 | 2 |
| 33.1 | 2.7 | 1 |
| 33.8 | 2.7 | 1 |

Figure 9:
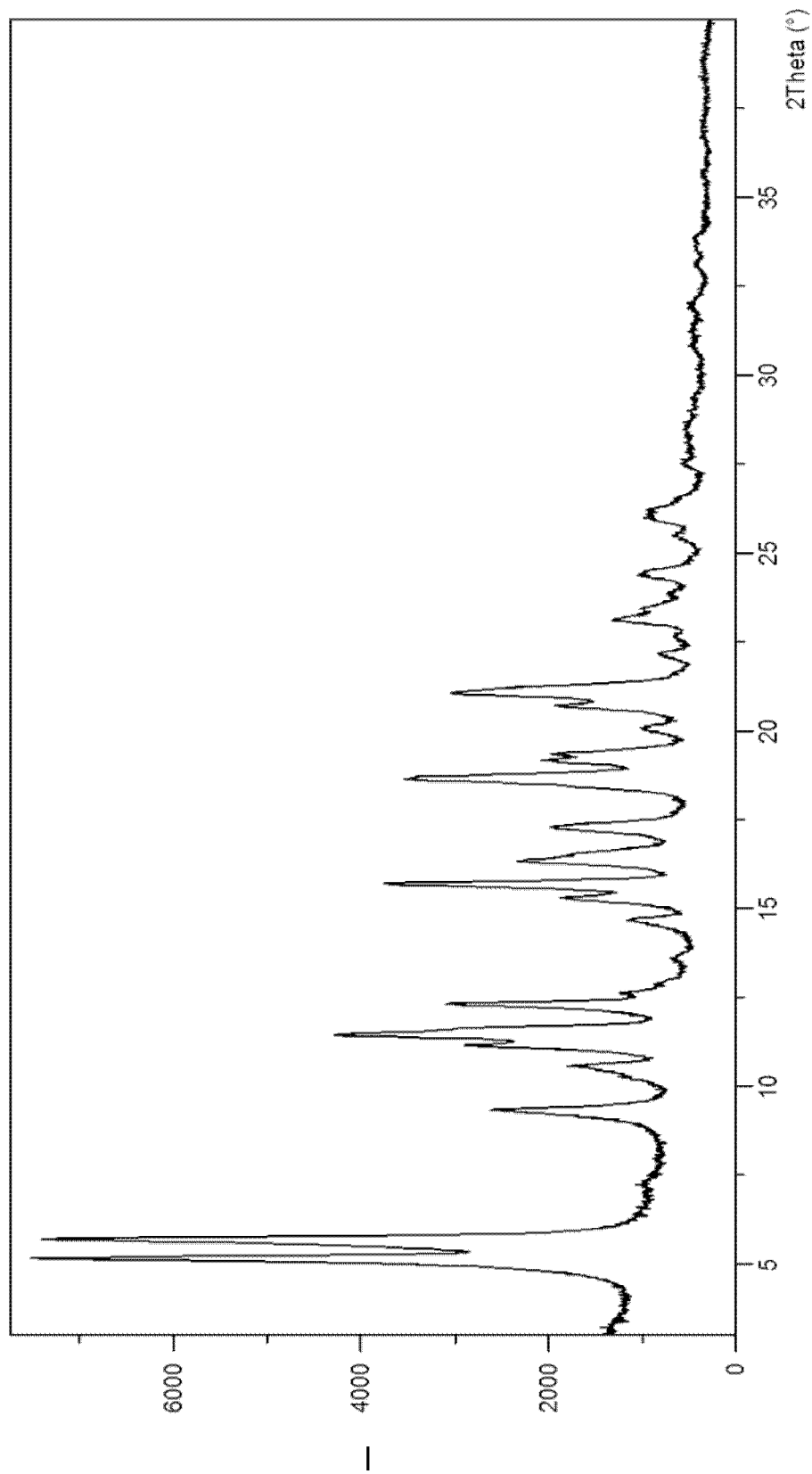
FIG. 9 shows the X-ray powder diffractogram (XRPD) of the cocrystal Form V. The spectrum expresses intensity (I; counts) versus degrees 2 theta (°).

The cocrystal Form V of the present invention may be further characterized by an X-ray diffractogram as in FIG. 9.

The cocrystal Form V of the present invention may also be further characterized by the following $^1$H NMR spectrum (CD$_3$OD, 400 MHz, δ): 6.08 (s, 2H, ArH); 5.29 (s, 1H); 4.45 (d, 2H, J=14.1 Hz); 3.99-3.90 (m, 2H); 3.42-3.35 (m, 1H); 3.26-3.19 (m, 1H); 2.94-2.87 (m, 1H); 2.38 (t, 2H, J=7.7 Hz); 2.35-2.25 (m, 1H); 2.24-2.08 (m, 2H); 2.02-1.92 (m, 3H); 1.77-1.71 (m, 2H); 1.68 (s, 3H); 1.64 (s, 3H); 1.59-1.51 (m, 2H); 1.39-1.25 (m, 4H); 0.90 (t, 3H, J=7.0 Hz).

Figure 10:
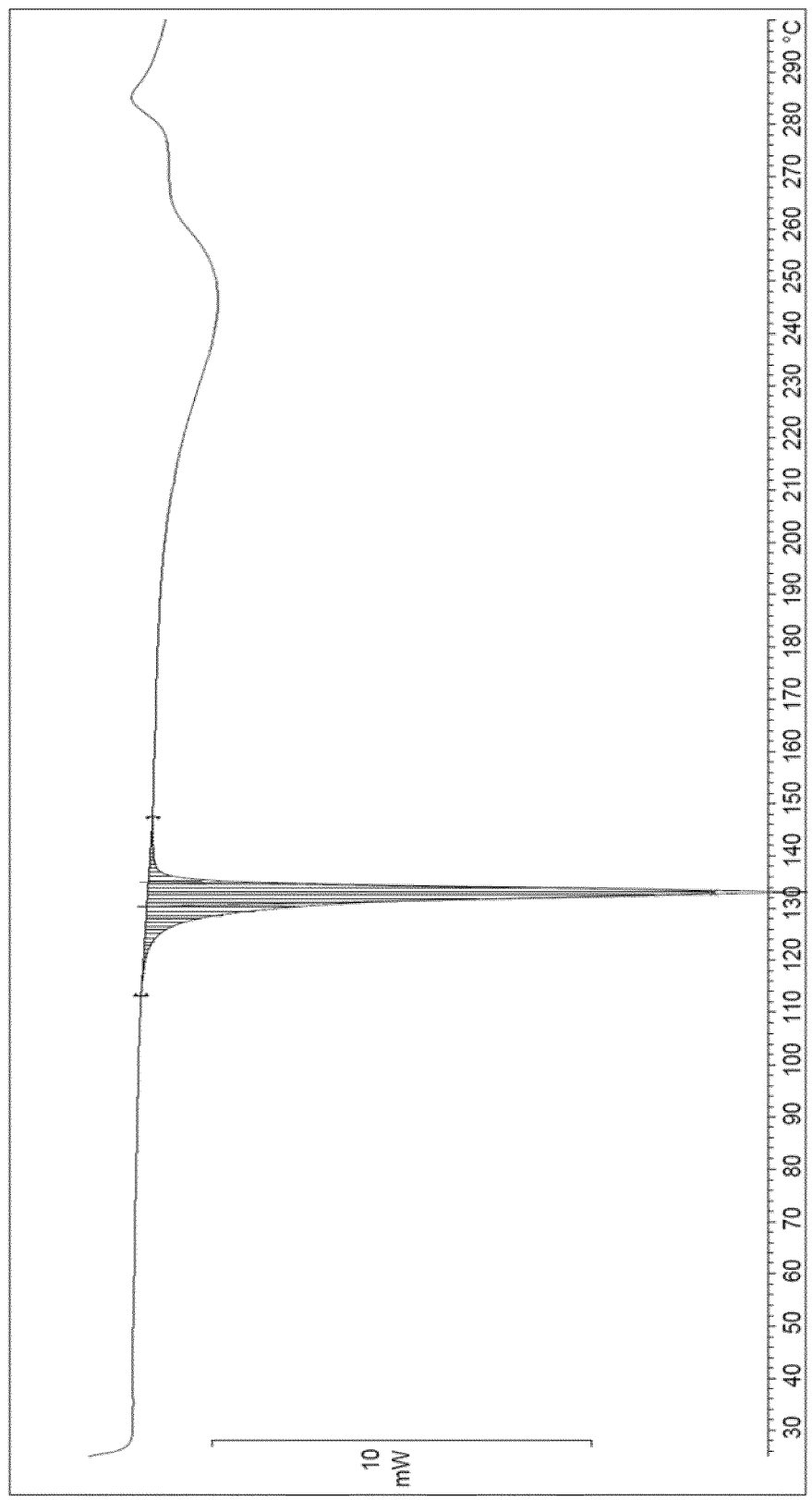
FIG. 10 shows the DSC of cocrystal Form V. The spectrum expresses the heat flow (mW/mg) versus temperature (C).

The cocrystal Form V of the present invention may also be further characterized by DSC (differential scanning calorimetry) analysis as shown in FIG. 10. The DSC analysis of cocrystal Form V shows an endothermic event with an onset at 130° C. which corresponds to the melting point of cocrystal Form V followed by endothermic and exothermic peaks possibly due to degradation (decomposition) events. The cocrystal Form V of the present invention may also be further characterized by having a melting range of 128-134° C.

The cocrystal of Form V of the present invention prepared from pure commercial CBD (98.6% a/a HPLC) has a purity similar to the starting material. It is worth noting that the coformer is not detected in the HPLC conditions used in this analysis.

The cocrystal Form V of the present invention is in a molar ratio 1:1 (CBD:DL-proline).

In an embodiment, the cocrystal of the invention is a cocrystal of CBD and (2S,3aS,7aS)-octahydro-1H-indole-2-carboxylic acid, also named Form VI. For the purposes of the invention, (2S,3aS,7aS)-octahydro-1H-indole-2-carboxylic acid has the CAS No. 80875-98-5. The structure of (2S,3aS,7aS)-octahydro-1H-indole-2-carboxylic acid is the following:

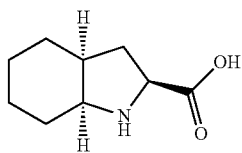 [SMILES: O=C(O)[C@@H]1C[C@@H]2CCCC[C@@H]2N1]

In an embodiment, the cocrystal Form VI of the present invention is characterized by having an X-ray powder diffractogram that comprises characteristic peaks at 4.4, 6.2 and 8.3±0.3 degrees 2 theta at a Cu—K$_\alpha$ radiation, λ=1.5406 Å. In an embodiment, the cocrystal Form VI of the present invention is characterized by having an X-ray powder diffractogram that comprises further characteristic peaks at 10.0, 13.3 and 16.0±0.3 degrees 2 theta at a Cu—K$_\alpha$ radiation, λ=1.5406 Å.

More specifically, the cocrystal Form VI of the present invention is characterized by exhibiting in the X-ray powder diffractogram a pattern of peaks, expressed in 2 theta units in degrees, 2θ (°), which is shown in Table 7.

TABLE 7

List of selected peaks (only peaks with relative intensity greater than or equal to 1% are indicated):

| Pos. [°2θ] | d-spacing [Å] | Rel. Int. [%] |
|---|---|---|
| 4.4 | 20.2 | 100 |
| 5.4 | 16.3 | 31 |
| 6.2 | 14.3 | 68 |
| 8.3 | 10.7 | 39 |
| 8.8 | 10.1 | 33 |
| 10.0 | 8.8 | 88 |
| 10.9 | 8.1 | 12 |
| 11.3 | 7.8 | 19 |
| 12.4 | 7.1 | 31 |
| 13.3 | 6.6 | 29 |
| 13.9 | 6.4 | 11 |
| 14.3 | 6.2 | 9 |
| 15.4 | 5.8 | 8 |
| 16.0 | 5.5 | 64 |
| 16.6 | 5.4 | 47 |
| 17.6 | 5.0 | 32 |
| 18.2 | 4.9 | 61 |
| 18.7 | 4.7 | 3 |
| 19.1 | 4.6 | 5 |
| 19.5 | 4.5 | 19 |
| 20.2 | 4.4 | 8 |
| 20.6 | 4.3 | 24 |
| 21.0 | 4.2 | 4 |
| 21.5 | 4.1 | 8 |
| 21.7 | 4.1 | 12 |
| 22.0 | 4.0 | 9 |
| 22.6 | 3.9 | 7 |
| 22.9 | 3.9 | 18 |

TABLE 7-continued

List of selected peaks (only peaks with relative intensity greater than or equal to 1% are indicated):

| Pos. [°2θ] | d-spacing [Å] | Rel. Int. [%] |
|---|---|---|
| 23.8 | 3.7 | 8 |
| 24.3 | 3.7 | 15 |
| 25.0 | 3.6 | 5 |
| 25.4 | 3.5 | 5 |
| 25.8 | 3.5 | 7 |
| 26.6 | 3.4 | 2 |
| 28.1 | 3.2 | 3 |
| 28.7 | 3.1 | 3 |
| 29.1 | 3.1 | 3 |
| 29.8 | 3.0 | 4 |
| 31.1 | 2.9 | 2 |
| 32.1 | 2.8 | 2 |
| 33.9 | 2.6 | 1 |
| 35.6 | 2.5 | 1 |
| 37.1 | 2.4 | 2 |

Figure 12:
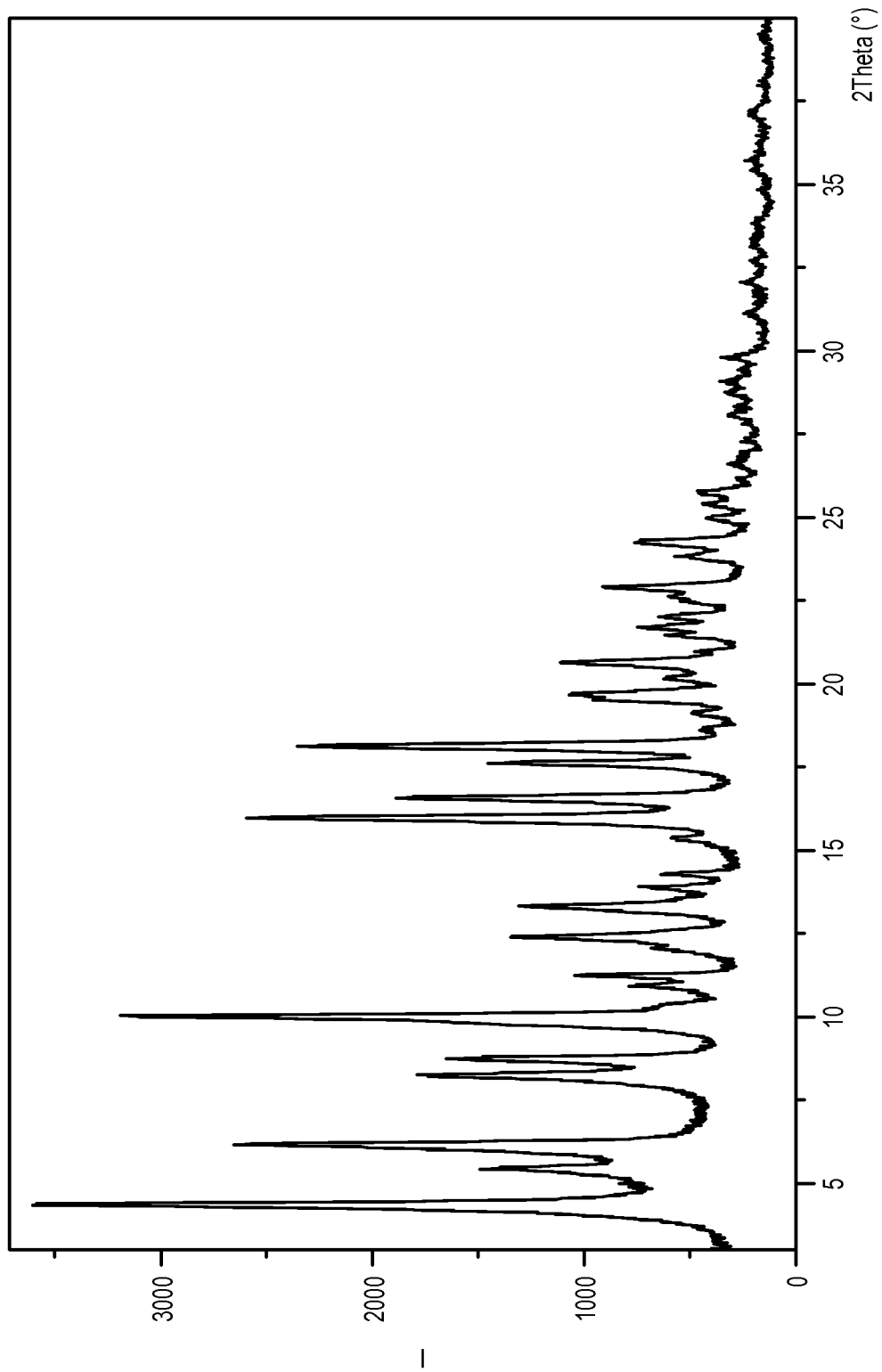
FIG. 12 shows the X-ray powder diffractogram (XRPD) of the cocrystal Form VI. The spectrum expresses intensity (I; counts) versus degrees 2 theta (°).

The cocrystal Form VI of the present invention may be further characterized by an X-ray diffractogram as in FIG. 12.

The cocrystal Form VI of the present invention may also be further characterized by the following $^1$H NMR spectrum (CD$_3$OD, 400 MHz, δ): 6.08 (s, 2H, ArH); 5.29 (s, 1H); 4.45 (d, 2H, J=14.2 Hz); 4.01-3.91 (m, 2H); 3.67-3.63 (m, 1H); 2.94-2.87 (m, 1H); 2.41-2.31 (m, 4H); 2.27-2.15 (m, 1H); 2.12-2.05 (m, 1H); 2.04-1.96 (m, 1H); 1.93-1.84 (m, 1H); 1.81-1.61 (m, 11H); 1.59-1.25 (m, 10H); 0.90 (t, 3H, J=7.0 Hz).

Figure 13:
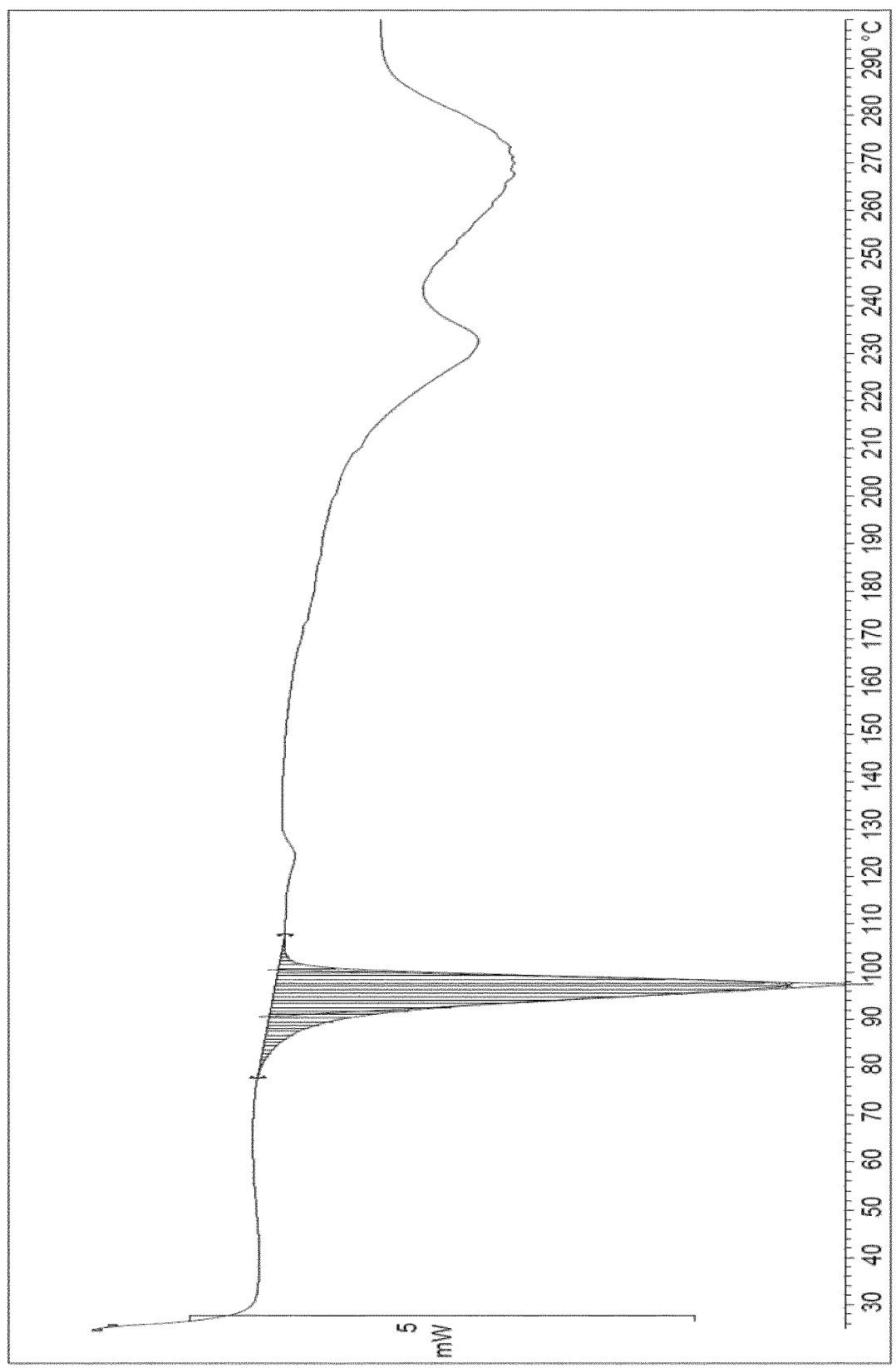
FIG. 13 shows the DSC of cocrystal Form VI. The spectrum expresses the heat flow (mW/mg) versus temperature (C).

The cocrystal Form VI of the present invention may also be further characterized by DSC (differential scanning calorimetry) analysis as shown in FIG. 13. The DSC analysis of cocrystal Form VI shows an endothermic event with an onset at 91° C. which corresponds to the melting point of cocrystal Form VI followed by endothermic peaks possibly due to degradation (decomposition) events. The cocrystal Form VI of the present invention may also be further characterized by having a melting range of 90-100° C.

The cocrystal of Form VI of the present invention prepared from pure commercial CBD (98.6% a/a HPLC) has a purity similar to the starting material. It is worth noting that the coformer is not detected in the HPLC conditions used in this analysis.

The cocrystal Form VI of the present invention is in a molar ratio 1:1 (CBD:(2S,3aS,7aS)-octahydro-1H-indole-2-carboxylic acid).

The second aspect of the invention is the provision of processes for the preparation of the cocrystal of the invention as defined above. The cocrystal of CBD and a co-former of the invention may be prepared as a pure form or as a mixture by two different processes.

Thus, a process for the preparation of the cocrystal of the present invention comprises: (a) wet grinding a mixture of CBD and the co-former in a solvent; and (b) drying the cocrystal thus obtained.

In an embodiment, step (a) is carried out in the presence of a solvent selected from the group consisting of water; an organic solvent selected from (C$_5$-C$_8$)alkane, (C$_1$-C$_4$)alcohol, (C$_1$-C$_4$)alkyl-CO—(C$_1$-C$_4$)alkyl, halogen-(C$_1$-C$_4$)alkane, (C$_1$-C$_4$)alkyl-CO—O—(C$_1$-C$_4$)alkyl, cyclo(C$_5$-C$_7$)alkane, phenyl-(C$_1$-C$_4$)alkyl, (C$_1$-C$_4$)—CN, H—CO—N((C$_1$-C$_4$)alkyl)$_2$; and mixtures thereof. The term "alcohol" refers to an "alkane" wherein at least one hydrogen atom is substituted by a hydroxyl group and which contains the number of carbon atoms specified in the description or claims. The term "alkane" refers to a saturated, branched or linear hydrocarbon which contains the number of carbon atoms specified in the description or claims. Examples include methanol, ethanol, n-propanol, iso-propanol, butanol, iso-butanol, and sec-butanol. The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl. The term "halogen-alkane" refers to an alkane in which at least one hydrogen atom is substituted by an halogen atom and which contains the number of carbon atoms specified in the description or claims. Examples of halogen-alkane include chloroform, trichloroethane and dichloroethane. The term cycloalkane refers to a "cyclic" alkane which contains the number of carbon atoms specified in the description or claims. The term cycloalkane includes carbocyclic alkanes or heterocyclic alkanes. The term "carbocyclic" alkane refers to a cyclic alkane being each member of the cycle a carbon atom. Examples of carbocyclic alkanes include cyclopentane and cyclohexane. The term "heterocyclic" alkane refers to a "carbocyclic" compound in which at least one carbon atom is substituted by a N, NH, O, or S atom. Examples of heterocyclic alkane include tetrahydrofuran and 1,4-dioxane.

In an embodiment, step (a) is carried out in the presence of an organic solvent selected from the group consisting of $(C_5$-$C_8)$alkane, $(C_1$-$C_4)$alcohol, $(C_1$-$C_4)$alkyl-CO—$(C_1$-$C_4)$alkyl, halogen-$(C_1$-$C_4)$alkane, $(C_1$-$C_4)$alkyl-CO—O—$(C_1$-$C_4)$alkyl, cyclo$(C_5$-$C_7)$alkane, phenyl-$(C_1$-$C_4)$alkyl, $(C_1$-$C_4)$—CN, H—CO—N$((C_1$-$C_4)$alkyl$)_2$ and mixtures thereof. This process is particularly advantageous because allows for obtaining the cocrystal in pure form.

In an embodiment, step (a) is carried out in the presence of heptane, water, acetonitrile, methanol, isobutylacetate, methylisobutylketone, dimethylformamide, 1,4-dioxane, dichloromethane, xylene, cyclohexane, and mixtures thereof.

In an embodiment, when the cocrystal is cocrystal Form I, then step (a) is performed in a solvent selected from the group consisting of water, acetonitrile, methanol, isobutylacetate, methylisobutylketone, dimethylformamide, 1,4-dioxane, dichloromethane, xylene, and mixtures thereof;

In an embodiment, when the cocrystal is cocrystal Form II, then step (a) is performed in a solvent selected from the group consisting of $(C_1$-$C_4)$alkyl-CO—$(C_1$-$C_4)$alkyl, $(C_1$-$C_4)$alkyl-CO—O—$(C_1$-$C_4)$alkyl, cyclo$(C_5$-$C_7)$alkane, phenyl-$(C_1$-$C_4)$alkyl, H—CO—N$((C_1$-$C_4)$alkyl$)_2$ and mixtures thereof. In an embodiment, step (a) is carried out in the presence of a solvent selected from the group consisting of isobutylacetate, methylisobutylketone, dimethylformamide, 1,4-dioxane, xylene, and mixtures thereof.

In an embodiment, when the cocrystal is cocrystal Form III, then the solvent of step (a) is cyclo$(C_5$-$C_7)$ alkane and mixtures thereof. In an embodiment, step (a) is cyclohexane and mixtures thereof.

In an embodiment, when the cocrystal is cocrystal Form IV, then the solvent of step (a) is $(C_1$-$C_{12})$ alkane and mixtures thereof. In an embodiment, step (a) is heptane and mixtures thereof.

In an embodiment, when the cocrystal is cocrystal Form V, then the solvent of step (a) is $(C_1$-$C_{12})$ alkane and mixtures thereof. In an embodiment, step (a) is heptane and mixtures thereof.

In an embodiment, when the cocrystal is cocrystal Form VI, then the solvent of step (a) is $(C_1$-$C_{12})$ alkane and mixtures thereof. In an embodiment, step (a) is heptane and mixtures thereof.

In an embodiment, in step (a) of the process for the preparation of the cocrystal of the present invention, the molar ratio between the CBD and the coformer is comprised from 2:1 to 1:2; preferably 1:1.

In an embodiment, step (a) is carried out at room temperature. In another embodiment, step (a) is carried out under vibrational milling, particularly at a power comprised from 15 Hz to 60 Hz; preferably comprised from 20 and 50 Hz; more preferably comprised from 25 and 35 Hz, particularly 30 Hz.

In an embodiment, step (b) is carried out by drying the cocrystal thus obtained at room temperature, preferably under vacuum conditions. Generally, the vacuum involves a pressure comprised from 0.5 mbar to 3 mbar; preferably comprised from 1 to 2 mbar.

An alternative process for the preparation of the cocrystal of the present invention comprises: (c) slurrying the CBD with a coformer and an organic solvent; and (d) isolating the cocrystal thus obtained.

In an embodiment, step (c) is carried out in the presence of a solvent selected from the group consisting of $(C_1$-$C_4)$ alcohol, $(C_1$-$C_4)$alkyl-CO—$(C_1$-$C_4)$alkyl, halogen-$(C_1$-$C_4)$ alkane, $(C_1$-$C_4$alkyl-CO—O—$(C_1$-$C_4)$alkyl, cyclo$(C_5$—C) alkane, phenyl-$(C_1$-$C_4)$alkyl, $(C_5$-$C_8)$alkane, and mixture thereof. In an embodiment, step (c) is carried out in the presence of a solvent selected from the group consisting of cyclohexane, ethanol, isopropylalcohol, ethylacetate, acetone, methyl isobutyl ketone, tetrahydrofuran, methyl tert-butyl ether, dichloromethane, heptane, and toluene.

In an embodiment, when the cocrystal is cocrystal Form I, then step (c) is performed in a solvent selected from the group consisting of cyclohexane, ethanol, isopropylalcohol, ethylacetate, acetone, methyl isobutyl ketone, tetrahydrofuran, methyl tert-butyl ether, dichoromethane, heptane, and toluene; preferably cyclohexane and heptane.

In an embodiment, when the cocrystal is cocrystal Form II, then step (c) is performed in a solvent selected from the group consisting of $(C_1$-$C_4)$alcohol, cyclo$(C_5$-$C_7)$ alkane, $(C_1$-$C_8)$alkane and mixtures thereof. In an embodiment, step (c) is carried out in the presence of a solvent selected from the group consisting of isopropanol and heptane and mixtures thereof; preferably heptane.

In an embodiment, when the cocrystal is cocrystal Form III, then step (c) is performed in a solvent selected from the group consisting of cyclo$(C_5$-$C_7)$ alkane, $(C_1$-$C_8)$alkane and mixtures thereof; preferably cyclohexane and heptane.

In an embodiment, when the cocrystal is cocrystal Form IV, then step (c) is performed in a solvent selected from the group consisting of cyclo$(C_5$-$C_7)$ alkane, $(C_1$-$C_8)$alkane and mixtures thereof; preferably heptane.

In an embodiment, when the cocrystal is cocrystal Form V, then step (c) is performed in a solvent selected from the group consisting of cyclo$(C_5$-$C_7)$ alkane, $(C_1$-$C_8)$alkane and mixtures thereof; preferably heptane.

In an embodiment, when the cocrystal is cocrystal Form VI, then step (c) is performed in a solvent selected from the group consisting of cyclo$(C_5$-$C_7)$ alkane, $(C_1$-$C_8)$alkane and mixtures thereof; preferably heptane.

In an embodiment, in step (c) of the process for the preparation of the cocrystal of the present invention, the molar ratio between the CBD and the coformer is comprised from 2:1 to 1:3; preferably comprised from 1:1 to 1:2. In a particular embodiment, when the cocrystal is cocrystal Form I, then the molar ratio between the CBD and the coformer is 1:1. In a particular embodiment, when the cocrystal is cocrystal Form II, then the molar ratio between the CBD and the coformer is 1:1. In a particular embodiment, when the cocrystal is cocrystal Form III, then the molar ratio between the CBD and the coformer is 1:2. In a particular embodiment, when the cocrystal is cocrystal Form IV, then the molar ratio between the CBD and the coformer is 1:1. In a particular embodiment, when the cocrystal is cocrystal Form V, then the molar ratio between the CBD and the coformer is 1:1. In a particular embodiment, when the cocrystal is cocrystal Form VI, then the molar ratio between the CBD and the coformer is 1:1.

In an embodiment, step (c) is carried out at room temperature. In another embodiment, step (c) is maintained under stirring overnight.

In an embodiment, the isolation step (d) may include removing the solvent, for example, by one or more of the following operations: filtration, filtration under vacuum, decantation, and centrifuge, or other suitable techniques as known to a person skilled in the art.

Preferably, step (d) is carried out by filtration of the solid followed by a washing step; preferably with water. In an embodiment, step (d) further comprises drying the isolated cocrystal; preferably the cocrystal is dried at room temperature, preferably under vacuum conditions. Generally, the vacuum involves a pressure comprised from 0.5 mbar to 3 mbar.

In a particular embodiment, the mixture of step (a), or alternatively step (c) is seeded to start the crystallization. In an embodiment, step (a), or alternatively step (c) is seeded with the cocrystal of the invention, particularly cocrystal Form I, cocrystal Form II, cocrystal Form III, cocrystal Form IV, cocrystal Form V and cocrystal Form VI. The seeding cocrystal form may be obtained by wet grinding process.

The third aspect of the invention relates to a process for the purification of CBD which comprises (e) dissociating a cocrystal as defined above, particularly cocrystal Form I, Form IV and Form V, more particularly cocrystal Form I and Form V, under such reaction conditions to obtain CBD; and (f) isolating the CBD thus obtained.

In an embodiment, the purification process further comprises previous steps of preparing the cocrystal by the process as defined above in the second aspect of the invention comprising performing steps (c) and (d). All embodiments disclosed above for steps (c) and (d) also apply in the process for the purification of CBD of the third aspect of the invention.

In an embodiment, step (e) is carried out by dissolving the cocrystal of the present invention in a mixture of water and one or more water-immiscible organic solvent and subsequent separation of the phases of the biphasic mixture. The term "immiscible organic solvent" refers to an organic solvent that, when combined, forms two phases, which means that the mixture thus obtained is "biphasic" under specified conditions of component concentrations and temperature among others. Further, the term "water-immiscible organic solvent" refers to an organic solvent that can form a biphasic phase with water at the temperature at which the reaction is carried out. As used herein, the term "biphasic" refers to a reaction medium that includes two immiscible liquid phases, for example, an aqueous phase and a water-immiscible organic solvent phase. The term "biphasic" can also be used to describe a method employing such a reaction medium. In an embodiment, in step (e) the water-immiscible organic solvent is selected from the group consisting of $(C_1-C_9)$alkane, $(C_1-C_4)$alkyl-O—$(C_1-C_4)$alkyl and mixtures thereof; preferably $(C_1-C_9)$alkane. Examples of $(C_1-C_9)$ alkane include, among others, heptane, cyclohexane, pentane and mixtures thereof.

Isolation step (f) may include removing the solvent by evaporation to dryness or isolating the CBD after crystallization, for example, by one or more of the following operations: filtration, filtration under vacuum, decantation, and centrifuge, or other suitable techniques as known to a person skilled in the art. In an embodiment, step (f) further comprises drying the isolated CBD; preferably the cocrystal is dried at room temperature, preferably under vacuum conditions. Generally, the vacuum involves a pressure comprised from 0.5 mbar to 3 mbar.

The fourth aspect of the invention relates to a pharmaceutical composition comprising a pharmaceutically effective amount of a cocrystal of CBD and a "pharmaceutically acceptable coformer" as defined above; particularly the cocrystals Form I, Form II, Form III, Form IV, Form V and Form VI together with one or more appropriate acceptable excipients or carriers.

The term "pharmaceutical composition" refers to a cocrystal disclosed herein with other chemical components, such as diluents or carriers. The pharmaceutical composition facilitates administration of the cocrystal of the present invention to an organism.

The term "pharmaceutically effective amount" refers to the amount of the cocrystal which provides a therapeutic effect after its application. In an embodiment, the "pharmaceutically effective amount of the cocrystal" refers to the amount of the cocrystal which provides after its dissociation after administration a therapeutically effective amount of CBD.

The terms "pharmaceutically acceptable excipients or carriers" refers to acceptable material, composition or vehicle, such as liquid or solid filler, diluent, excipient, solvent, or encapsulating material. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio.

The compositions of the invention can be formulated in several forms that include, but are not limited to, oral, topical, transdermal and parenteral compositions.

In an embodiment, the composition of the invention is an oral composition which comprises appropriate excipients or carriers for oral administration including, but not limited to, binder, lubricant, surfactant and diluent. The oral compositions can be formulated in several forms that include, but are not limited to solutions, tablets, capsules, granules, suspensions, dispersions, powders, lozenges, concentrates, drops, elixirs, emulsions, pastilles, pellets and spray. In an embodiment, the composition of the invention is in the form of drops, spray and capsules.

The compositions of the present invention can be prepared according to methods well known in the state of the art. The appropriate excipients and/or carriers, and their amounts, can readily be determined by those skilled in the art according to the type of formulation being prepared.

The fifth aspect of the invention relates to a cocrystal of CBD and a coformer as defined above for use as a medicament; particularly cocrystals Form I, Form II, Form III, Form IV, Form V and Form VI. An embodiment refers to use of the cocrystal of CBD as defined above as an anti-inflammatory, antipsychotic and anticonvulsant agent. This aspect could also be formulated as the use of the cocrystal of CBD and a coformer as defined in the first aspect of the invention; particularly cocrystals Form I, Form II, Form III, Form IV, Form V and Form VI for the preparation of a medicament for the prophylaxis and/or treatment of a disease or condition which occurs with inflammation, psychosis or convulsions as defined above. It also relates to a method for the prophylaxis and/or treatment of a mammal suffering, or susceptible to suffer, from a disease or condition which occurs with inflammation, psychosis or convulsions as defined above, wherein the method comprises administering to said mammal an effective amount of the cocrystal of CBD and a coformer as defined in the present invention; particularly cocrystals Form I, Form II, Form III, Form IV, Form V and Form VI together with one or more acceptable excipients or carriers.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

General Considerations

Proton nuclear magnetic resonance analysis were recorded in deuterated solvents in a Varian Mercury 400 MHz spectrometer, equipped with a broadband probe ATB 1H/19F/X of 5 mm. Spectra were acquired dissolving the sample in 0.7 mL of deuterated solvent.

X-ray power Diffraction (XRPD) measurements were performed at ambient conditions on a PANalytical X'Pert PRO 0-0 diffractometer of 240 mm of radius in reflection geometry, equipped with Cu K$\alpha$ radiation and a PIXcel detector, operated at 45 kV and 40 mA. Each sample was mounted on a zero-background silicon holder and allowed to spin at 0.25 rev/s during the data collection. The measurement angular range was 3.0-40.0° (2θ) with a step size of 0.013° and a scanning speed 0.328°/s (10.20 s/step) for the cocrystal forms of the present invention and 3.0-30.0° (2θ) with a step size of 0.0130 and a scanning speed 0.082°/s (40.80 s/step) for commercial CBD used as starting material and purified CBD obtained after dissociating the cocrystal of the present invention.

DSC analyses were recorded with a Mettler Toledo DSC2. The sample (4.0200 mg of cocrystal Form I, 3.2500 mg of cocrystal Form II and 3.56 mg of cocrystal Form III) was weighed into a 40 µL aluminium crucible with a pinhole lid and was heated from 25 to 300° C. at a rate of 10° C./min, under nitrogen (50 mL/min).

HPLC analyses were recorded in an Agilent 1100 HPLC system equipped with a vacuum degasser (G1322A), a quaternary pump (G1311A), an autosampler (G1313A) and a VW detector (G1314A). Column Zorbax Eclipse XDB-C18 150×4.6 mm, 5 µm was used. The sample (5 mg) was dissolved in methanol (5 mL) and injected (1 µL) for HPLC measurement in isocratic conditions (ACN:water 80:20) with the detector measuring at 225 nm.

Thermogravimetric analysis (TGA) was recorded in a thermogravimetric analyzer Mettler Toledo TGA/SDTA851$^e$. The sample (4.5290 mg of cocrystal Form 1) was weighed into a 100 µL alumina crucible and sealed with a lid. The lid was automatically punched by the robot just before the analysis. Samples were heated at 10° C./min from 25 to 300° C., under nitrogen (50 mL/min).

CBD starting material obtained by an extractive process used in sections 1.1.A, 1.1.B.1, 1.2. and 1.3. is commercially available (CBDepot s.r.o.). Cannabis sativa fraction containing about 50% w/w of CBD used as starting material in section 1.2.B.2. was is also commercially available (CBDepot s.r.o.).

1. Cocrystal of CBD and a Zwitterionic Coformer
1.1. Cocrystal Form I
Preparation Process
A. Preparation by Wet Grinding To a 2 mL Eppendorf tube containing CBD (20 mg, 0.064 mmol, 98.8% a/a HPLC), L-Proline (7.3 mg, 0.064 mmol, 1 eq.), 2 drops of acetonitrile and three stainless steel grinding balls were added before milling for 45 minutes at a rate of 30 Hz (3 cycles of 15 minutes) with a Retsch Ball Mill MM 400. After drying under vacuum (approx. 1-2 mbar) at room temperature cocrystal Form I of the present invention was obtained as a white solid.

B. Preparation by Slurrying
B.1. Preparation of Cocrystal Form I by Slurrying from High Purity CBD To a round-bottomed flask equipped with magnetic stirring and $N_2$ atmosphere, containing a mixture of CBD (1.00 g, 3.18 mmol, 1.5 eq., 98.8% a/a HPLC) and L-proline (244 mg, 2.120 mmol), was added heptane (20 mL). The resulting mixture was seeded with CBD-L-Proline Form I and stirred at room temperature for 15 hours. Then, the reaction was monitored by XRPD analysis and an additional amount of CBD (584 mg, 1.85 mmol, 0.87 eq.) was added until complete conversion of L-proline was observed. The suspension was filtered through a sinter funnel (porosity no 3) and washed with 3×3.0 mL of heptane. After drying under vacuum at room temperature, cocrystal Form I of the present invention was obtained as a white solid (662 mg, 31%).

Figure 2:
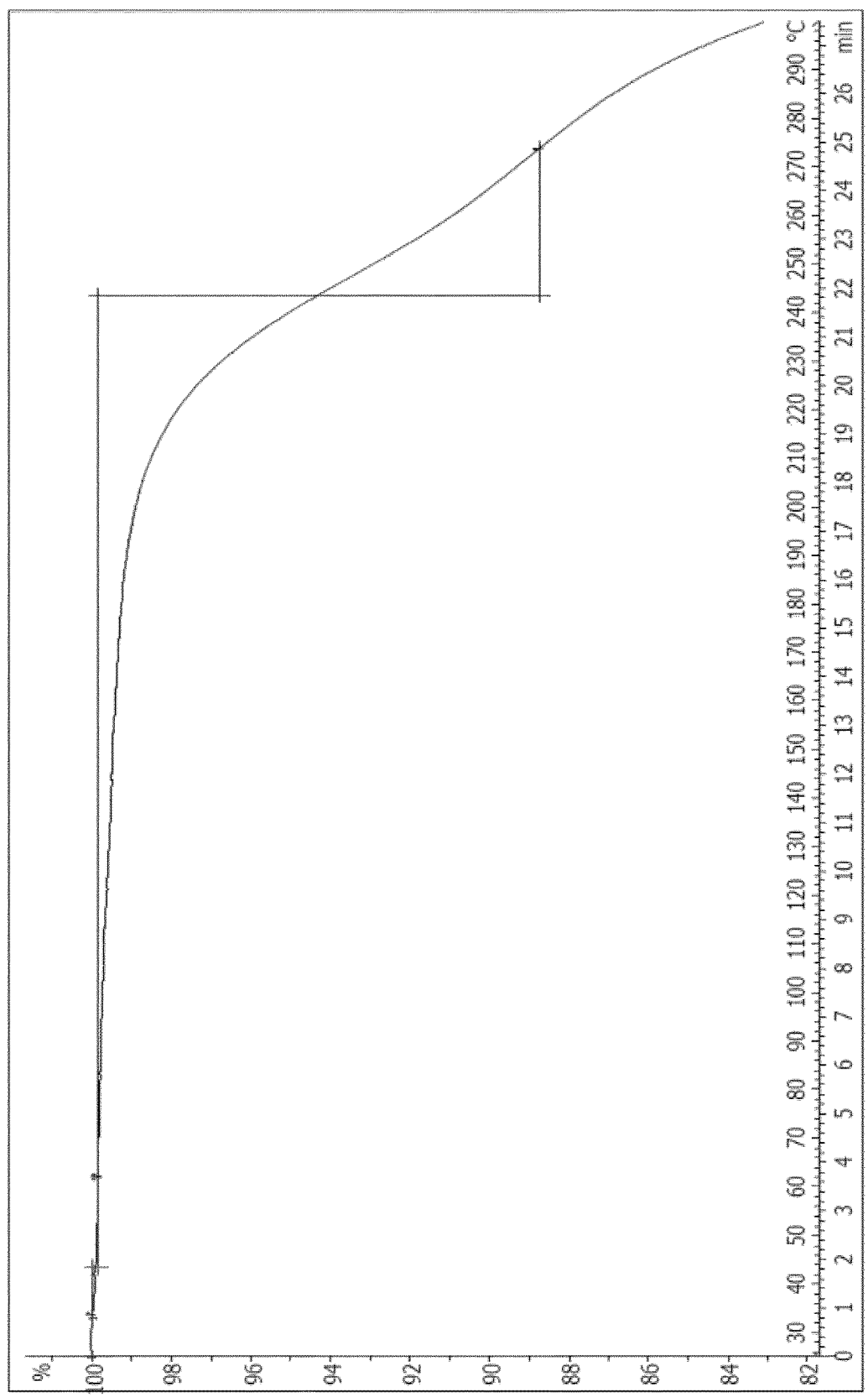
FIG. 2 shows the TGA of cocrystal Form I. The thermogram expresses weight loss (% w/w) versus temperature (° C.).

The cocrystal Form I thus obtained shows an X-ray powder diffractogram (XRPD) as in FIG. 1, a TGA as in FIG. 2. The cocrystal Form I thus obtained also shows the $^1$H NMR and the DSC spectra disclosed above. The TGA shows that it is not a stoichiometric hydrate.

B.2. Purification Process of CBD from Cannabis sativa Flower Extract by Cocrystallization of Form I
Preparation of Cocrystal Form I To a round-bottomed flask equipped with magnetic stirring and $N_2$ atmosphere, containing a mixture of Cannabis sativa flower fraction about 50% w/w CBD (100 mg, 0.159 theoretical mmol) and L-proline (18.3 mg, 0.159 mmol), was added heptane (1 mL). The resulting mixture was seeded with the cocrystal Form I of the present invention and stirred at room temperature for 15 h. The suspension was filtered through a sinter funnel (porosity n° 3) and washed with 3×0.2 mL of heptane. After drying under vacuum at room temperature, cocrystal Form I containing traces of L-proline was obtained as a white solid (51 mg).

Dissociation of CBD from Cocrystal Form I

The cocrystal Form I thus obtained was dissolved in 5 mL of a mixture of heptane:water (1:1), the heptane phase was washed with water (2×1 mL) and dried with anhydrous $Na_2SO_4$ before eliminating the solvent under reduced pressure and vacuum. Thus, CBD was recovered as a white pasty solid (35 mg, 35% overall yield from a maximum of 50% yield, 99.4% a/a HPLC).

Figure 6:
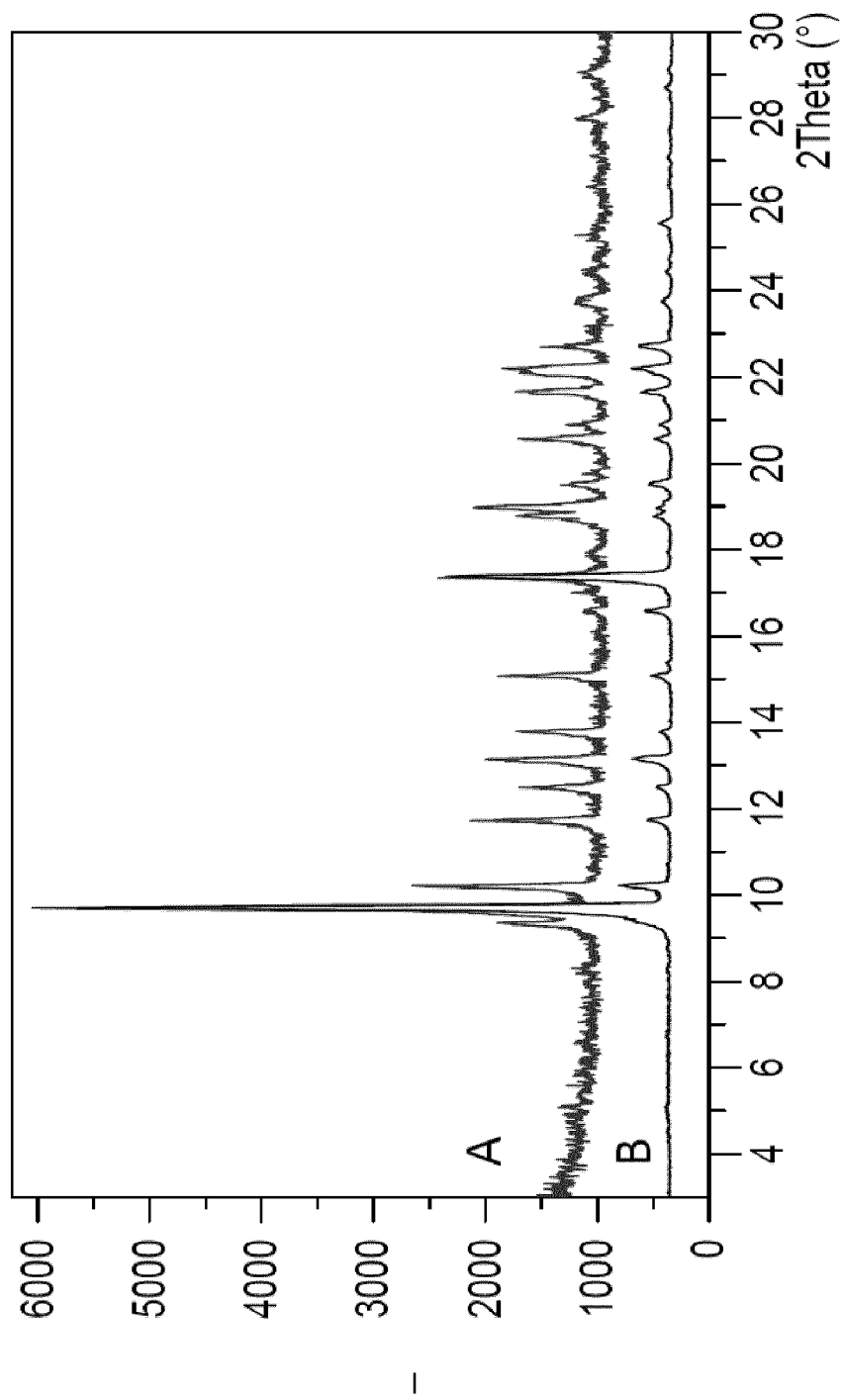
FIG. 6 shows the X-ray powder diffractogram (XRPD) of pure commercially available CBD (diffractogram B) and the X-ray powder diffractogram (XRPD) of CBD isolated from the cocrystal Form I obtained in Example 1.1.B.2. (diffractogram A). The spectrum expresses intensity (I; counts) versus degrees 2 theta (°).

CBD thus obtained shows an X-ray powder diffractogram (XRPD) identical to pure commercial CBD in FIG. 6. Comparison of the $^1$H NMR spectra and HPLC analyses between *Cannabis sativa* flower extract containing about 50% w/w of CBD used as starting material and CBD recovered from the cocrystallisation of Form I (Example 1.1.B.2.) purification process indicates an excellent purification (see also section 2 below).

1.2. Cocrystal Form II
Preparation Process
A. Preparation by Wet Grinding

To a 2 mL Eppendorf tube containing CBD (20 mg, 0.064 mmol, 98.8% a/a HPLC), betaine (9.3 mg, 0.064 mmol, 1 eq.), 2 drops of isobutylacetate and three stainless steel grinding balls were added before milling for 45 minutes at a rate of 30 Hz (3 cycles of 15 minutes) with a Retsch Ball Mill MM 400. After a drying under vacuum (approx. 1-2 mbar) at room temperature, cocrystal Form II of the present invention was obtained as a white solid (quantitative yield).

B. Preparation by Slurrying

To a closed tube equipped with magnetic stirring and $N_2$ atmosphere, containing a mixture of CBD (50 mg, 0.159 mmol, 2 eq., 98.8% a/a HPLC) and betaine (9.3 mg, 0.080 mmol), was added heptane (0.5 mL). The resulting mixture was seeded with cocrystal Form II and stirred at room temperature for 15 hours. The suspension was filtered through a sinter funnel (porosity n° 3) and washed with 2×0.1 mL of heptane. After drying under vacuum at room temperature, cocrystal Form II was obtained as a white solid (34 mg, 50%).

The cocrystal Form II thus obtained shows an X-ray powder diffractogram (XRPD) as in FIG. 3; and it also shows the $^1$H NMR and the DSC spectra disclosed above.

1.3. Cocrystal Form III
Preparation Process
A. Preparation by Wet Grinding

To a 2 mL Eppendorf tube containing CBD (20 mg, 0.064 mmol), L-carnitine (10.3 mg, 0.064 mmol, 1 eq.), 2 drops of cyclohexane and three stainless steel grinding balls were added before milling for 45 minutes at a rate of 30 Hz (3 cycles of 15 minutes) with a Retsch Ball Mill MM 400. After a drying under vacuum (approx. 1-2 mbar) at room temperature, pure cocrystal Form III was obtained as a white solid.

B. Preparation by Slurrying

To a round-bottomed flask equipped with magnetic stirring containing a mixture of CBD (300 mg, 0.954 mmol, 98.8% a/a HPLC) and L-carnitine (307 mg, 1.908 mmol, 2 eq.), was added heptane (3 mL). The resulting mixture was seeded with cocrystal Form III and stirred at room temperature for 15 hours. The suspension was filtered through a sinter funnel (porosity no 3) and washed with 2×1.0 mL of heptane. After drying under vacuum at room temperature, cocrystal Form III was obtained as a white solid (483 mg, 80%).

The cocrystal Form III thus obtained shows an X-ray powder diffractogram (XRPD) as in FIG. 4; and it also shows the $^1$H NMR and DSC spectra disclosed above.

1.4. Cocrystal Form IV
Preparation Process by Slurrying from High Purity CBD

To a cylindrical vial equipped with magnetic stirring and $N_2$ atmosphere, containing a mixture of CBD (399 mg, 1.269 mmol, 2 eq.) and D-proline (74 mg, 0.643 mmol), was added heptane (4 mL). The resulting mixture was stirred at room temperature overnight. Then, additional heptane was added (4 mL) because solvent had almost completely evaporated. The suspension was filtered through a sinter funnel (porosity n° 3) and washed with 3×0.4 mL of heptane. After drying under vacuum at room temperature, cocrystal Form IV of the present invention was obtained as a white solid (264 mg, 48%).

The cocrystal Form IV thus obtained shows an X-ray powder diffractogram (XRPD) as in FIG. 7; and it also shows the $^1$H NMR and DSC spectra disclosed above.

1.5. Cocrystal Form V
Preparation Process by Slurrying from High Purity CBD

To a cylindrical vial equipped with magnetic stirring and $N_2$ atmosphere, containing a mixture of CBD (399 mg, 1.269 mmol, 2 eq.) and DL-proline (74 mg, 0.643 mmol), was added heptane (4 mL). The resulting mixture was stirred at room temperature overnight. Then, additional heptane was added (3 mL) because solvent had partially evaporated. The suspension was filtered through a sinter funnel (porosity no 2) and washed with 3×0.4 mL of heptane. After drying under vacuum at room temperature, cocrystal Form V of the present invention was obtained as a white solid (252 mg, 46%).

The cocrystal Form V thus obtained shows an X-ray powder diffractogram (XRPD) as in FIG. 9; and it also shows the $^1$H NMR and DSC spectra disclosed above.

1.5. Cocrystal Form VI
Preparation Process by Slurrying from High Purity CBD

To a test tube equipped with magnetic stirring, containing a mixture of CBD (79 mg, 0.251 mmol, 3 eq.) and (2S,3aS,7aS)-octahydro-1H-indole-2-carboxylic acid (14 mg, 0.084 mmol), was added heptane (0.55 mL). The resulting mixture was stirred at room temperature overnight. The suspension was filtered through a sinter funnel (porosity n° 3) and washed with 3×0.08 mL of heptane. After drying under vacuum at room temperature, cocrystal Form VI (possibly contaminated with (2S,3aS,7aS)-octahydro-1H-indole-2-carboxylic acid) of the present invention was obtained as a white solid (25.2 mg, 48%).

The cocrystal Form VI thus obtained shows an X-ray powder diffractogram (XRPD) as in FIG. 12, a DSC as in FIG. 13. The cocrystal Form VI thus obtained also shows the $^1$H NMR disclosed below.

2. CBD Purification Study

The aim of this study is the measurement of the purity of the cocrystals of CBD of the present invention and the comparison with the purity of the CBD samples used as starting material and the CBD resulting from purification by cocrystallisation of the cocrystal Form 1.

2.1. Samples

Sample 1: Commercial *Cannabis Sativa* flower extract containing 50% by weight of CBD in relation to the total weight of the extract.

Sample 2: Pure commercial CBD used as starting material in the CBD cocrystal preparation.

Sample 3: Pure CBD obtained from *Cannabis Sativa* flower extract after purification by cocrystallization of Form I and the subsequent cocrytal dissociation step.

2.2. Method

Each sample (5 mg) was dissolved in methanol (5 mL) and injected (1 μL) for HPLC measurement in isocratic conditions (acetonitrile:water 80:20) with the detector measuring at 225 nm.

2.3. Results

The purity and the impurity profile of the CBD used as a starting material (Sample 1 and Sample 2) and that obtained after purification of Sample 1 (Sample 3) are disclosed in Table 4A. The purity and the impurity profile of the cocrystals Form I and Form II of the present invention prepared from Sample 1 are disclosed in Table 4B.

The purity of the starting materials, the cocrystals of the present invention, and the CBD obtained after dissociation of the cocrystals of the present invention as well as the amount of the impurities are expressed in area %.

TABLE 4A

| CBD sample | Purity (Area %) | Impurity profile (Area %) | | |
|---|---|---|---|---|
| | | Cannabidivarin | CBD C4 analogue[2] | THC[3] |
| Sample 1 | 98.00[1] | 0.88 | 0.28 | ND[4] |
| Sample 2 | 98.83 | 0.66 | 0.22 | 0.03 |
| Sample 3 | 99.66 | ND[4] | 0.16 | ND[4] |

[1]Most of the impurities are not detected by HPLC.
[2]CBD C4 analogue corresponds to 2-[(1R,6R)-6-isopropenyl-3-methylcyclohex-2-en-1-yl]-5-butylbenzene-1,3-diol.
[3]THC corresponds to tetrahydrocannabinol.
[4]ND stands for not detected.

TABLE 4B

| Cocrystal of the invention | Starting compound | Purity (Area %) | Impurity profile (Area %) | | |
|---|---|---|---|---|---|
| | | | Cannabidivarin | CBD C4 analogue[1] | THC[2] |
| Cocrystal Form I | Sample 1 | 99.26 | ND[4] | 0.19 | ND[5] |
| Cocrystal Form I | Sample 2 | 99.03[3] | 0.41 | 0.15 | 0.01 |
| Cocrystal Form II | Sample 2 | 99.03[4] | 0.50 | 0.28 | 0.02 |

[1]CBD C4 analogue corresponds to 2-[(1R,6R)-6-isopropenyl-3-methylcyclohex-2-en-1-yl]-5-butyllbenzene-1,3-diol.
[2]THC corresponds to tetrahydrocannabinol.
[3]Under the HPLC conditions, L-proline of cocrystal Form I is not detected.
[4]Under the HPLC conditions, betaine of cocrystal Form II is not detected.
[5]ND stands for not detected.

As shown in the Table above, the preparation of the cocrystals of the present invention allows for purifying the CBD, and especially crude CBD, with a less laborious, less expensive and more readily scalable process compared to the state of the art. The preparation of the cocrystals of the present invention allows for purifying the CBD when the CBD used as starting material has a purity about 50% w/w and even when the starting CBD already has high purity (about 98 area %), particularly cocrystals Form I and Form II.

Figure 5:
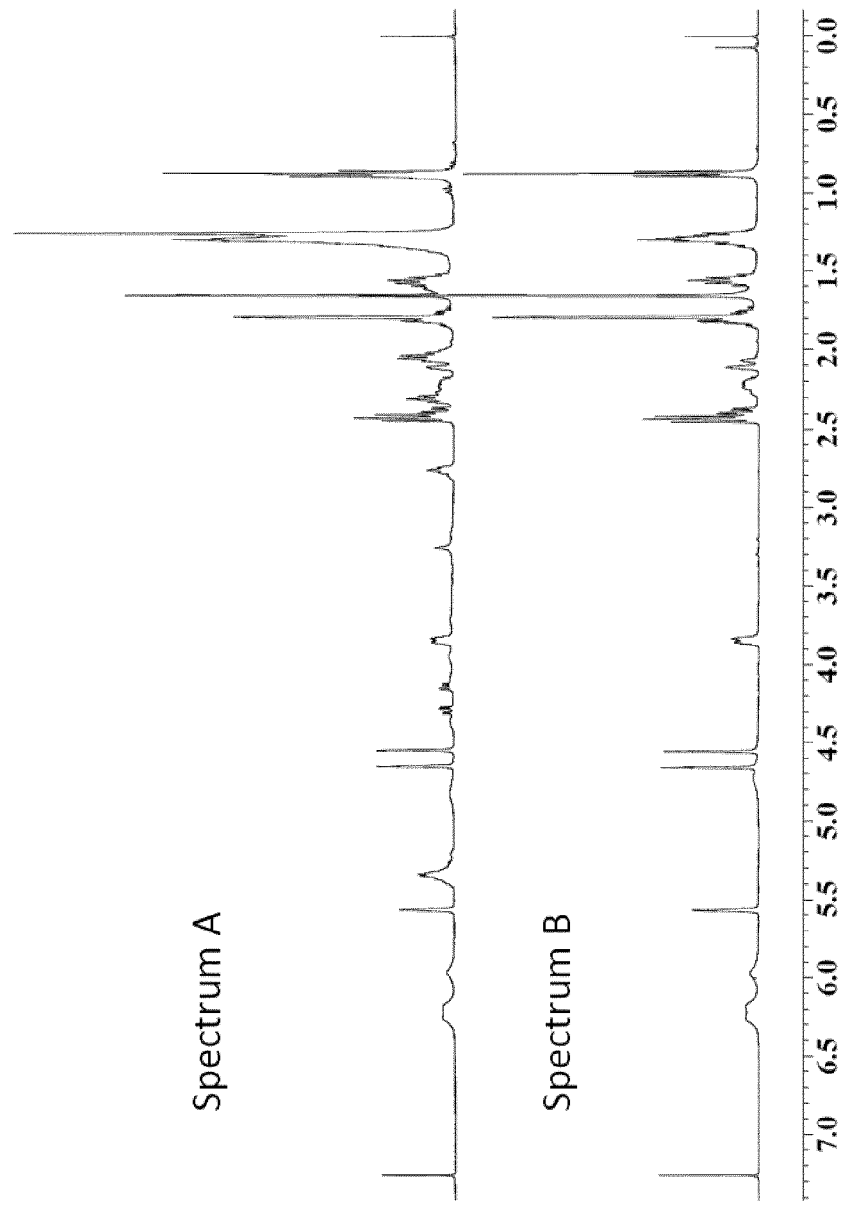
FIG. 5 shows the 1H NMR spectrum of the *Cannabis sativa* flower extract containing 50% w/w of CBD (sample 1) used as starting material in Example 1.1.B.2 (Spectrum A) and the 1H NMR spectrum of the CBD recovered after dissociation of the cocrystal Form I obtained in Example 1.1.B.2 (Spectrum B).

Dissociation of Form I obtained from Sample 1 in a biphasic heptane/water mixture led to CBD (Sample 3) with a slightly higher purity (99.66% a/a) than Form I (99.26% a/a), a significantly higher purity than Sample 1 (50% purity by weight, 98.00 a/a) and an overall yield of 35% (comprising cocrystallization and cocrystal dissociation steps from a maximum of 50% yield). Furthermore, the 1H NMR analysis shows that the coformers and impurities not detectable by UV are removed (see FIG. 5), the HPLC analysis shows that the impurities detectable by UV are also reduced. In fact, cannabidivarin is reduced from 0.88% a/a to a non-detectable amount and the CBD C4 analogue is reduced from 0.28% to 0.16% a/a, and XRPD analysis indicates the same crystalline form as commercial pure CBD (FIG. 6).

Furthermore, the preparation of the cocrystals from Sample 2 of the present invention also allows for reducing the amount of all the identified impurities. Particularly, the amount of THC is reduced by half.

3. Stability Study

The aim of the study is to evaluate the stability of cocrystal Form I of the present invention.

3.1. Sample

Cocrystal Form I of the present invention obtained by the process disclosed in section 1.1.B.1.

3.2. Method

Cocrystal Form I (55 mg) is stored in an open vial and exposed to accelerated stability conditions (40° C. and 75±5% relative humidity) according to ICH guidelines (Guidance for Industry Q1A(R2) Stability Testing of New Drug Substances and Products—available on the website http://www.ich.org/products/guidelines/quality/quality-single/article/stability-testing-of-new-drug-substances-and-products.html on Aug. 4, 2017).

3.3. Results

Under the above mentioned conditions, cocrystal Form I of the present invention remained stable for at least three weeks.

CITATION LIST

1 T. Petrzilka et al. "synthese und chiralität des (−)-cannabidiols vorlsufige mitteilung". Helvetica Chimica Acta. 1967, vol. 50(2), pp. 719-23.
2 T. Petrzilka et al. "synthese von haschisch-inhaltsstoffen. 4. Mitteilung". Helvetica Chimica Acta. 1969, vol. 52(4), pp. 1102-34.
3. P. G. Jones, et al. "Cannabidiol". Acta Crystallographica Section B. 1977, B33, p. 3211-3214.
4. Seung-HwaBaek et al. "Boron triflouride etherate on alimina—a modified Lewis acid reagent: An improved synthesis of cannabidiol". Tetrahedron letters. 1985, vol. 26(8), pp. 1083-1086.
5. Q1A(R2) Stability Testing of New Drug Substances and Products—available on the website http://www.ich.org/products/guidelines/quality/quality-single/article/stability-testing-of-new-drug-substances-and-products.html on Aug. 4, 2017
6. WO2009018389.
7. WO2006133941.
8. WO2007041167.
9. WO2015032519.

The invention claimed is:

1. A cocrystal of 2-[(1R,6R)-6-isopropenyl-3-methylcyclohex-2-en-1-yl]-5-pentylbenzene-1,3-diol and a zwitterion coformer, wherein the cocrystal is selected from the group consisting of:

a cocrystal of 2-[(1R,6R)-6-isopropenyl-3-methylcyclohex-2-en-1-yl]-5-pentylbenzene-1,3-diol and L-proline characterized by having an X-ray diffractogram that comprises characteristic peaks at 5.8, 11.1 and 15.8±0.3 degrees 2 theta at a Cu-K$_\alpha$radiation, λ=1.5406 Å;

a cocrystal of 2-[(1R,6R)-6-isopropenyl-3-methylcyclohex-2-en-1-yl]-5-pentylbenzene-1,3-diol and betaine characterized by having an X-ray diffractogram that comprises characteristic peaks at 9.1, 10.7 and 18.4±0.3 degrees 2 theta at a Cu-K$_\alpha$radiation, λ=1.5406 Å;

a cocrystal of 2-[(1R,6R)-6-isopropenyl-3-methylcyclohex-2-en-1-yl]-5-pentylbenzene-1,3-diol and L-carnitine characterized by having an X-ray diffractogram that comprises characteristic peaks at 6.8, 11.3 and 20.0±0.3 degrees 2 theta at a Cu-K$_\alpha$radiation, λ=1.5406 Å;

a cocrystal of 2-[(1R,6R)-6-isopropenyl-3-methylcyclohex-2-en-1-yl]-5-pentylbenzene-1,3-diol and DL-proline characterized by having an X-ray diffractogram that comprises characteristic peaks at 5.7, 11.1 and 15.7±0.3 degrees 2 theta at a Cu-K$_\alpha$radiation, λ=1.5406 Å; and a cocrystal of 2-[(1R,6R)-6-isopropenyl-3-methylcyclohex-2-en-1-yl]-5-pentylbenzene-1,3-diol and (2S,3aS,7aS)-octahydro-1H-indole-2-carboxylic acid characterized by having an X-ray diffractogram that comprises characteristic at 4.4, 6.2 and 8.3±0.3 degrees 2 theta at a Cu-K$_\alpha$radiation, λ=1.5406 Å.

2. The cocrystal according to claim 1, which is a cocrystal of 2-[(1R,6R)-6-isopropenyl-3-methylcyclohex-2-en-1-yl]-5-pentylbenzene-1,3-diol and L-proline characterized by having an X-ray diffractogram that comprises characteristic peaks at 5.8, 11.1 and 15.8±0.3 degrees 2 theta at a Cu-K$_\alpha$radiation, λ=1.5406 Å.

3. The cocrystal according to claim 2, which is characterized by further comprising characteristic peaks in the X-ray powder diffractogram at 7.4, 11.4 and 21.2±0.3 degrees 2 theta at a Cu-K$_\alpha$radiation, λ=1.5406 Å.

4. The cocrystal according to claim 1, which is a cocrystal of 2-[(1R,6R)-6-isopropenyl-3-methylcyclohex-2-en-1-yl]-5-pentylbenzene-1,3-diol and betaine characterized by having an X-ray diffractogram that comprises characteristic peaks at 9.1, 10.7 and 18.4±0.3 degrees 2 theta at a Cu-K$_\alpha$radiation, λ=1.5406 Å.

5. The cocrystal according to claim 4, which is characterized by further comprising characteristic peaks in the X-ray powder diffractogram at 5.3 and 13.0±0.3 degrees 2 theta at a Cu-K$_\alpha$radiation, λ=1.5406 Å.

6. The cocrystal according to claim 1, which is a cocrystal of 2-[(1R,6R)-6-isopropenyl-3-methylcyclohex-2-en-1-yl]-5-pentylbenzene-1,3-diol and L-carnitine characterized by having an X-ray diffractogram that comprises characteristic peaks at 6.8, 11.3 and 20.0±0.3 degrees 2 theta at a Cu-K$_\alpha$radiation, λ=1.5406 Å.

7. The cocrystal according to claim 6, which is characterized by further comprising characteristic peaks in the X-ray powder diffractogram at 12.7, 13.6, and 15.6 and ±0.3 degrees 2 theta at a Cu-K$_\alpha$radiation, λ=1.5406 Å.

8. The cocrystal according to claim 1, which is a cocrystal of 2-[(1R,6R)-6-isopropenyl-3-methylcyclohex-2-en-1-yl]-5-pentylbenzene-1,3-diol and DL-proline characterized by having an X-ray diffractogram that comprises characteristic peaks at 5.7, 11.1 and 15.7±0.3 degrees 2 theta at a Cu-K$_\alpha$radiation, λ=1.5406 Å.

9. The cocrystal according to claim 8, which is characterized by further comprising characteristic peaks in the X-ray powder diffractogram at 11.4 and 21.0±0.3 degrees 2 theta at a Cu-K$_\alpha$radiation, λ=1.5406 Å.

10. The cocrystal according to claim 1, which is a cocrystal of 2-[(1R,6R)-6-isopropenyl-3-methylcyclohex-2-en-1-yl]-5-pentylbenzene-1,3-diol and (2S,3aS,7aS)-octahydro-1H-indole-2-carboxylic acid characterized by having an X-ray diffractogram that comprises characteristic at 4.4, 6.2 and 8.3±0.3 degrees 2 theta at a Cu-K$_\alpha$radiation, λ=1.5406 Å.

11. The cocrystal according to claim 10, which is characterized by further comprising characteristic peaks in the X-ray powder diffractogram at 10.0, 13.3 and 16.0±0.3 degrees 2 theta at a Cu-K$_\alpha$radiation, λ=1.5406 Å.

12. A process for the preparation of the cocrystal selected from the group consisting of:

a) a cocrystal of 2-[(1R,6R)-6-isopropenyl-3-methylcyclohex-2-en-1-yl]-5-pentylbenzene-1,3-diol and L-proline characterized by having an X-ray diffractogram that comprises characteristic peaks at 5.8, 11.1 and 15.8±0.3 degrees 2 theta at a Cu-K$_\alpha$radiation, λ=1.5406 Å; a cocrystal of 2-[(1R,6R)-6-isopropenyl-3-methylcyclohex-2-en-1-yl]-5-pentylbenzene-1,3-diol and betaine characterized by having an X-ray diffractogram that comprises characteristic peaks at 9.1, 10.7 and 18.4±0.3 degrees 2 theta at a Cu-K$_\alpha$radiation, λ=1.5406 Å; a cocrystal of 2-f(1R,6R)-6-isopropenyl-3-methylcyclohex-2-en-1-yl]-5-pentylbenzene-1,3-diol and L-carnitine characterized by having an X-ray diffractogram that comprises characteristic peaks at 6.8, 11.3 and 20.0±0.3 degrees 2 theta at a Cu-K$_\alpha$radiation, λ=1.5406 Å; a cocrystal of 2-[(1R,6R)-6-isopropenyl-3-methylcyclohex-2-en-1-yl]-5-pentylbenzene-1,3-diol and DL-proline characterized by having an X-ray diffractogram that comprises characteristic peaks at 5.7, 11.1 and 15.7±0.3 degrees 2 theta at a Cu-K$_\alpha$radiation, λ=1.5406 Å; a cocrystal of 2-[(1R,6R)-6-isopropenyl-3-methylcyclohex-2-en-1-yl]-5-pentylbenzene-1,3-diol and (2S,3aS,7aS)-octahydro-1H-indole-2-carboxylic acid characterized by having an X-ray diffractogram that comprises characteristic at 4.4, 6.2 and 8.3±0.3 degrees 2 theta at a Cu-K$_\alpha$radiation, λ=1.5406 Å; and b) a cocrystal of 2-[(1R,6R)-6-isopropenyl-3-methylcyclohex-2-en-1-yl]-5-pentylbenzene-1,3-diol and D-proline characterized by having an X-ray diffractogram that comprises characteristic peaks at 5.7, 11.2 and 15.7±0.3 degrees 2 theta at a Cu-K$_\alpha$radiation, λ=1.5406 Å;

wherein:

when the cocrystal is a cocrystal as defined in a), then the process comprises:

(c) slurrying the 2-[(1R,6R)-6-isopropenyl-3-methylcyclohex-2-en-1-yl]-5-pentylbenzene-1,3-diol with the zwitterion coformer and an organic solvent; and (d) isolating the cocrystal thus obtained; and when the cocrystal is the cocrystal of 2-[(1R,6R)-6-isopropenyl-3-methylcyclohex-2-en-1-yl]-5-pentylbenzene-1,3-diol and D-proline, then the process comprises:

(c) slurrying the 2-[(1R,6R)-6-isopropenyl-3-methylcyclohex-2-en-1-yl]-5-pentylbenzene-1,3-diol with the zwitterion conformer D-proline and the organic solvent heptane; and (d) isolating the cocrystal thus obtained.

13. A process for the purification of 2-[(1R,6R)-6-isopropenyl-3-methylcyclohex-2-en-1-yl]-5-pentylbenzene-1,3-diol which comprises:

(e) dissociating a cocrystal selected from the group consisting of a cocrystal of 2-[(1R,6R)-6-isopropenyl-3-methylcyclohex-2-en-1-yl]-5-pentylbenzene-1,3-diol and L-proline characterized by having an X-ray diffractogram that comprises characteristic peaks at 5.8, 11.1 and 15.8±0.3 degrees 2 theta at a Cu-K$_\alpha$radiation, λ=1.5406 Å; a cocrystal of 2-[(1R,6R)-6-isopropenyl-3-methylcyclohex-2-en-1-yl]-5-pentylbenzene-1,3-diol and betaine characterized by having an X-ray diffractogram that comprises characteristic peaks at 9.1, 10.7 and 18.4±0.3 degrees 2 theta at a Cu-K$_\alpha$radiation, λ=1.5406 Å; a cocrystal of 2-[(1R, 6R)-6-isopropenyl-3-methylcyclohex-2-en-1-0]-5-pentylbenzene-1,3-diol and L-carnitine characterized by having an X-ray diffractogram that comprises characteristic peaks at 6.8, 11.3 and 20.0±0.3 degrees 2 theta at a Cu-K$_\alpha$ radiation, λ=1.5406 Å; a cocrystal of 2-[(1R,6R)-6-isopropyl-3-methylcyclohex-2-en-1-yl]-5-pentylbenzene-1,3-diol and DL-proline characterized by having an X-ray diffractogram that comprises characteristic peaks at 5.7, 11.1 and 15.7±0.3 degrees 2 theta at a Cu-K$_\alpha$ radiation, λ=1.5406 Å; a cocrystal of 2-[(1R,6R)-6-isopropyl-3-methylcyclohex-2-en-1-yl]-5-pentylbenzene-1,3-diol and (2S,3aS,7aS)-octahydro-1H-indole-2-carboxylic acid characterized by having an X-ray diffractogram that comprises characteristic at 4.4, 6.2 and 8.3±0.3 degrees 2 theta at a Cu-K$_\alpha$ radiation, λ=1.5406 Å; and a cocrystal of 2-[(1R,6R)-6-isopropyl-3-methylcyclohex-2-en-1-yl]-5-pentylbenzene-1,3-diol and D-proline characterized by having an X-ray diffractogram that comprises characteristic peaks at 5.7, 11.2 and 15.7±0.3 degrees 2 theta at a Cu-K$_\alpha$ radiation, λ=1.5406 Å;

under such reaction conditions to obtain 2-[(1R,6R)-6-isopropyl-3-methylcyclohex-2-en-1-yl]-5-pentyl-benzene-1,3-diol; and (f) isolating 2-[(1R,6R)-6-isopropyl-3-methylcyclohex-2-en-1-yl]-5-pentylbenzene-1,3-diol thus obtained.

14. The process according to claim 13, further comprising steps (c) and (d) before steps (e) and (f), comprising:

(c) slurrying the 2-[(1R,6R)-6-isopropyl-3-methylcyclohex-2-en-1-yl]-5-pentylbenzene-1,3-diol with the zwitterion coformer and an organic solvent; and (d) isolating the cocrystal thus obtained.

15. A pharmaceutical composition comprising a pharmaceutically effective amount of the cocrystal of 2-[(1R,6R)-6-isopropyl-3-methylcyclohex-2-en-1-yl]-5-pentylbenzene-1,3-diol and a pharmaceutically acceptable zwitterion coformer as defined in claim 1 together with one or more pharmaceutically acceptable excipients or carriers.

16. A cocrystal of 2-[(1R,6R)-6-isopropyl-3-methylcyclohex-2-en-1-yl]-5-pentylbenzene-1,3-diol and a zwitterion coformer as defined in claim 1 for use as a medicament.

17. The process according to claim 13, wherein step e) is carried out by dissolving the cocrystal in a mixture of water and one or more water-immiscible organic solvent and subsequent separation of the phases of the biphasic mixture.

18. The process according to claim 17, wherein the water-immiscible organic solvent is selected from the group consisting of $(C_1-C_9)$alkane, $(C_1-C_4)$alkyl-O—$(C_1-C_4)$alkyl and mixtures thereof.

19. The process according to claim 17, wherein the water-immiscible organic solvent is $(C_1-C_9)$alkane.

20. The process according to claim 17, wherein the water-immiscible organic solvent is one or more $(C_1-C_9)$ alkanes selected from the group consisting of heptane, cyclohexane, pentane and mixtures thereof.

* * * * *

UNITED STATES PATENT AND TRADEMARK OFFICE
CERTIFICATE OF CORRECTION

PATENT NO. : 11,168,047 B2  
APPLICATION NO. : 16/636888  
DATED : November 9, 2021  
INVENTOR(S) : Alexander Christian Comely, Nicolas Tesson and Carmen Jiménez González Page 1 of 1

It is certified that error appears in the above-identified patent and that said Letters Patent is hereby corrected as shown below:

On the Title Page

Item (54) and in the Specification, Column 1, Lines 1-4:
Please change:
"COCRYSTAL OF 2-[(1R,6R)-6-ISOPROPENYL-3-METHYLCYCLOHEX-2-EN-1-YL]-5-PENTYLBENZENE-L,3-DIOL"
To:
--COCRYSTAL OF 2-[(1R,6R)-6-ISOPROPENYL-3-METHYLCYCLOHEX-2-EN-1-YL]-5-PENTYLBENZENE-1,3-DIOL--

Signed and Sealed this  
Fifteenth Day of March, 2022

Drew Hirshfeld  
*Performing the Functions and Duties of the  
Under Secretary of Commerce for Intellectual Property and  
Director of the United States Patent and Trademark Office*